(12) United States Patent
Amos et al.

(10) Patent No.: US 12,622,626 B2
(45) Date of Patent: May 12, 2026

(54) REDUCING NOISE OF INTRACARDIAC ELECTROCARDIOGRAMS USING AN AUTOENCODER AND UTILIZING AND REFINING INTRACARDIAC AND BODY SURFACE ELECTROCARDIOGRAMS USING DEEP LEARNING TRAINING LOSS FUNCTIONS

(71) Applicant: Biosense Webster (Israel) Ltd., Yokneam (IL)

(72) Inventors: Yariv Avraham Amos, Tzorit (IL); Matityahu Amit, Cohav-Yair zur-Yigal (IL); Liat Tsoref, Tel Aviv (IL); Stanislav Goldberg, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 326 days.

(21) Appl. No.: 17/337,295

(22) Filed: Jun. 2, 2021

(65) Prior Publication Data

US 2021/0378597 A1 Dec. 9, 2021

Related U.S. Application Data

(60) Provisional application No. 63/061,929, filed on Aug. 6, 2020, provisional application No. 63/034,694, filed on Jun. 4, 2020.

(51) Int. Cl.
*A61B 5/367* (2021.01)
*A61B 5/00* (2006.01)
(Continued)

(52) U.S. Cl.
CPC .............. *A61B 5/367* (2021.01); *A61B 5/318* (2021.01); *A61B 5/7203* (2013.01); *A61B 5/725* (2013.01);
(Continued)

(58) Field of Classification Search
CPC ....... A61B 5/367; A61B 5/318; A61B 5/7203; A61B 5/725; A61B 5/7267; A61B 5/346; G06F 2218/04; G06F 2218/12
See application file for complete search history.

(56) References Cited

U.S. PATENT DOCUMENTS 8,355,928 B2 1/2013 Spahn
10,438,354 B2 10/2019 Hsieh et al.
(Continued)

FOREIGN PATENT DOCUMENTS

EP 2945087 A2 11/2015
WO 2018/134143 A1 7/2018
(Continued)

OTHER PUBLICATIONS

Xiong, Peng et al., "ECG Signal Enhancement based on Improved Denoising Auto-Encoder", Engineering Application so fArtificial Intelligence, vol. 52, May 6, 2016, pp. 194-202.*
(Continued)

*Primary Examiner* — Manuel L Barbee
(74) *Attorney, Agent, or Firm* — VOLPE KOENIG

(57) ABSTRACT

A system and method include a memory storing processor executable code for a denoised autoencoder, and one or more processors coupled to the memory to execute the processor executable code to receive raw signal data comprising signal noise, encode, by the denoised autoencoder, the raw signal data by performing a denoising autoencoder operation to produce a latent representation, and decode, by the denoised autoencoder, the latent representation to produce clean signal data reconstructed without the signal noise. A first filter is applied to a signal to emphasize activity within the signal and to produce a first modified signal, a rectifier and a second filter are applied to the first modified signal to smooth areas of the first modified signal with clinical importance and to produce a second modified signal, and
(Continued)

FIG. 6B high frequency energy zones of the second modified signal are automatically detected using an energy threshold to produce a weights vector.

17 Claims, 15 Drawing Sheets

(51) Int. Cl.
    *A61B 5/318*       (2021.01)
    *G06F 18/214*     (2023.01)
(52) U.S. Cl.
    CPC .......... *A61B 5/7267* (2013.01); *G06F 18/214* (2023.01); *G06F 2218/04* (2023.01); *G06F 2218/12* (2023.01)

(56) References Cited

U.S. PATENT DOCUMENTS

| | | | |
|---|---|---|---|
| 10,573,031 | B2 | 2/2020 | Mailhe et al. |
| 11,977,998 | B2 | 5/2024 | Stiller et al. |
| 2008/0221830 | A1 | 9/2008 | Ilkin |
| 2011/0201900 | A1 | 8/2011 | Zhang et al. |
| 2012/0184865 | A1 | 7/2012 | Harlev et al. |
| 2013/0132117 | A1 | 5/2013 | Barsoum et al. |
| 2014/0330148 | A1 | 11/2014 | Ng |
| 2015/0105681 | A1 | 4/2015 | Bonan |
| 2015/0161535 | A1 | 6/2015 | Ptashek et al. |
| 2017/0202516 | A1* | 7/2017 | Bar-Tal ................. A61B 5/287 |
| 2018/0144246 | A1 | 5/2018 | Jayadeva |
| 2018/0146922 | A1 | 5/2018 | Wang |
| 2019/0139275 | A1 | 5/2019 | Hao |
| 2019/0142291 | A1* | 5/2019 | Obeid ................. A61B 5/7203 706/12 |
| 2020/0012889 | A1 | 1/2020 | Gupta et al. |
| 2020/0356846 | A1* | 11/2020 | Saripalli ............... G06N 3/045 |
| 2020/0364545 | A1* | 11/2020 | Shattil ...................... G06N 3/08 |
| 2022/0039882 | A1 | 2/2022 | Botzer et al. |
| 2022/0416937 | A1* | 12/2022 | Andrews .............. H04B 1/0003 |

FOREIGN PATENT DOCUMENTS

| | | |
|---|---|---|
| WO | WO2019216378 A1 | 11/2019 |
| WO | 2020/070519 A1 | 4/2020 |

OTHER PUBLICATIONS

Chiang, Hsin-Tien et al., "Noise Reduction in ECG Signals using Fully Convolutional Denoising Autoencoders", IEEE ACcess, vol. 7, pp. 60806-60813, 2019.*

Xiong, Peng et al., "ECG Signal Enhancement based on Improved Denoising Auto-Encoder", Engineering Applications of Artificial Intelligence, vol. 52, May 6, 2016, pp. 194-102.*

Hong, Shenda et al., "Opportunities and Challenges in Deep Learning Methods on Electrocardiogram Data: A Systematic Review", arXiv:2001.01550v1, Dec. 28, 2019.*

European Search Report for corresponding EPA No. 21177820.4 dated Jan. 31, 2022.

European Search Report for corresponding EPA No. 21177820.4 dated Nov. 9, 2021.

Singh Pratik et al., "A New ECG Denoising Framework Using Generative Adversarial Network", IEEE/ACM Transactions on Computational Biology and Bioinformatics, vol. 18, No. 2, Feb. 28, 2020, pp. 759-764.

Shenda Hong et al., "Opportunities and Challenges in Deep Learning Methods on Electrocardiogram Data: A Systematic Review", Dec. 28, 2019, p. 6, col. 1, paragragph 2.

Ansari Sardar et al., "A Review of Automated Methods for Detection of Myocardial Ischemia and Infarction Using Electrocardiogram and Electronic Health Records", IEEE Reviews in Biomedical Engineering, vol. 10, Oct. 1, 2017, pp. 264-298.

Extended European Search Report dated Dec. 10, 2021 for European Patent Application No. 21189767.3.

Kumarasinghe, K., et al., "eSPANNet: Evolving Spike Pattern Association Neural Network for Spike-based Supervised Incremental Learning and Its Application for Single-trial Brain Computer Interfaces," International Joint Conference on Neural Networks (IJCNN), Budapest, Hungary, (2019).

Extended European Search Report issued on Nov. 17, 2022 for European Patent Application No. 22194292.3.

United States Office Action issued on Jun. 12, 2025 for U.S. Appl. No. 17/443,774.

Ajmi, I., et al., "Mapping patient path in the Pediatric Emergency Department: A workflow model driven approach," Journal of Biomedical Informatics, vol. 54, 2015, pp. 315-328, ISSN 1532-0464, (Year: 2015).

Ahmad, S., et al., Workflow efficiency pilot study of Surgery Viewer: A secure hands-free intraoperative multimedia interface for Google Glass; SAGE Open Medicine. 2019; 7. (Year: 2019).

Muthalaly, R. G., et al., "Applications of Machine Learning in Cardiac Electrophysiology," Arrhythmia & Electrophysiology review vol. 9,2 (2020): 71-77 (Year: 2020).

Parchami, "Using deep autoencoders to learn robust domain-invariant representations for still-to-video face recognition," 2017 14th IEEE International Conference on Advanced Video and Signal Based Surveillance (AVSS), (Aug. 2017).

Japanese Office Action mailed Mar. 25, 2025 for Japanese Patent Application No. 2021-094238.

Feeny "Artificial Intelligence and Machine Learning in Arrhythmias and Cardiac Electrophysiology" (2020).

Corrado C, Williams S, Karim R, Plank G, O'Neill M, Niederer S. A work flow to build and validate patient specific left atrium electrophysiology models from catheter measurements. Med Image Anal. Jul. 2018;47:153-163. (Year: 2018).

Non-Final Office Action dated Mar. 19, 2026 for U.S. Appl. No. 17/443,774.

\* cited by examiner

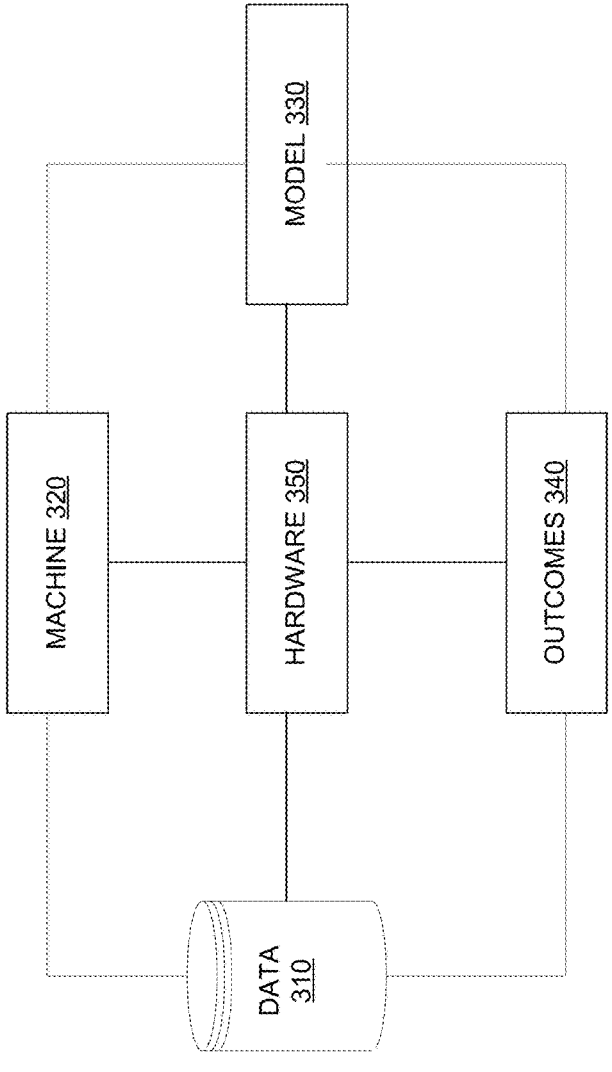
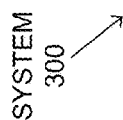
FIG. 3

METHOD 400

COLLECTING DATA FROM HARDWARE 410

TRAINING A MACHINE ON THE HARDWARE 420

BUILDING A MODEL 430

PREDICTING OUTCOMES OF THE HARDWARE 440

METHOD 500

APPLYING A FIRST FILTER TO A SIGNAL TO PRODUCE A FIRST MODIFIED SIGNAL
522

APPLYING A RECTIFIER AND A SECOND FILTER TO THE FIRST MODIFIED SIGNAL TO PRODUCE A SECOND MODIFIED SIGNAL
524

DETECTING HIGH FREQUENCY ENERGY ZONES TO PRODUCE A WEIGHTS VECTOR
526

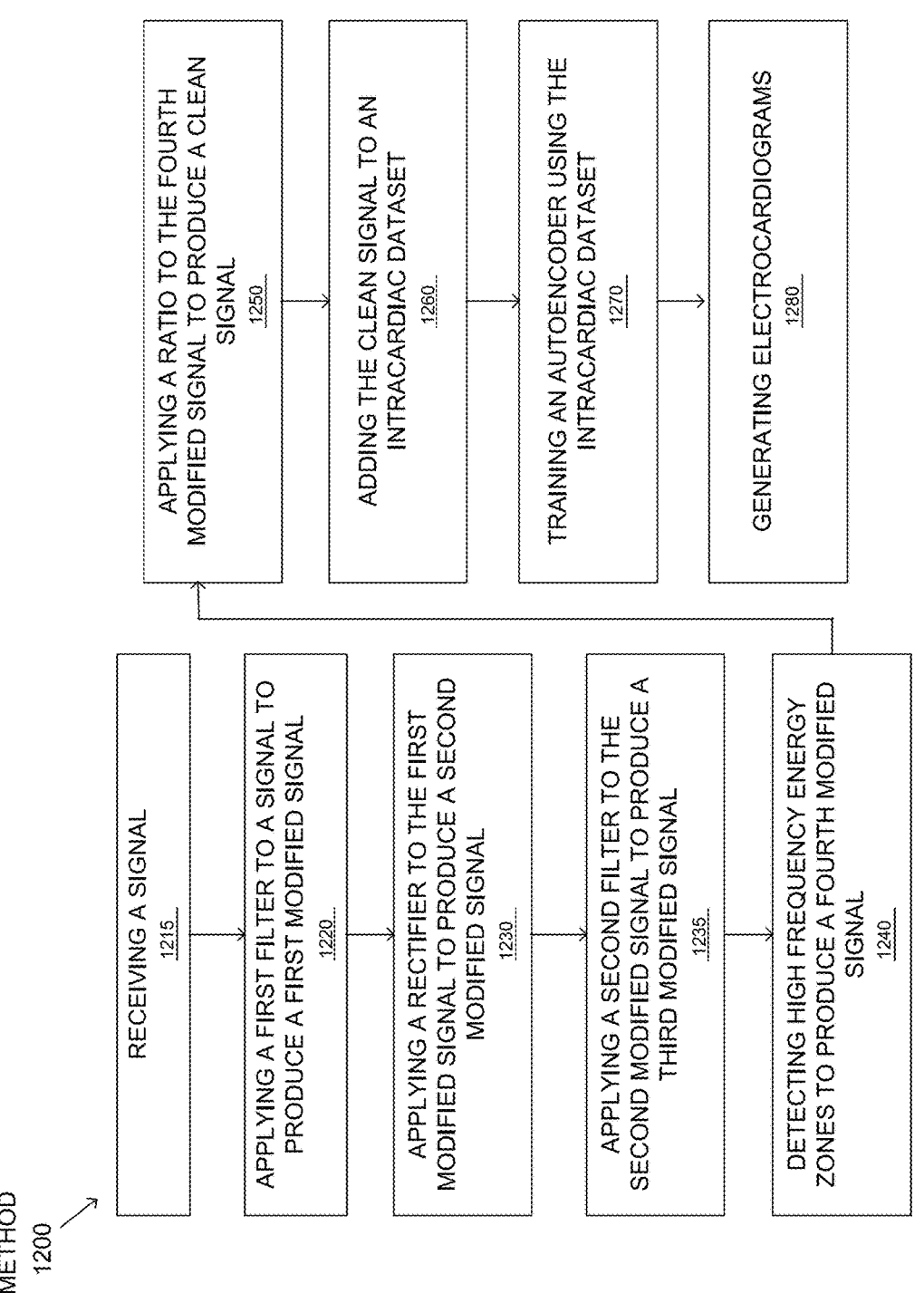

METHOD
1200

RECEIVING A SIGNAL
1215

APPLYING A FIRST FILTER TO A SIGNAL TO PRODUCE A FIRST MODIFIED SIGNAL
1220

APPLYING A RECTIFIER TO THE FIRST MODIFIED SIGNAL TO PRODUCE A SECOND MODIFIED SIGNAL
1230

APPLYING A SECOND FILTER TO THE SECOND MODIFIED SIGNAL TO PRODUCE A THIRD MODIFIED SIGNAL
1235

DETECTING HIGH FREQUENCY ENERGY ZONES TO PRODUCE A FOURTH MODIFIED SIGNAL
1240

APPLYING A RATIO TO THE FOURTH MODIFIED SIGNAL TO PRODUCE A CLEAN SIGNAL
1250

ADDING THE CLEAN SIGNAL TO AN INTRACARDIAC DATASET
1260

TRAINING AN AUTOENCODER USING THE INTRACARDIAC DATASET
1270

GENERATING ELECTROCARDIOGRAMS
1280

FIG. 12

REDUCING NOISE OF INTRACARDIAC ELECTROCARDIOGRAMS USING AN AUTOENCODER AND UTILIZING AND REFINING INTRACARDIAC AND BODY SURFACE ELECTROCARDIOGRAMS USING DEEP LEARNING TRAINING LOSS FUNCTIONS

CROSS REFERENCE TO RELATED APPLICATIONS

This application claims the benefit of U.S. Provisional Patent Application No. 63/034,694 (JNJBIO-6332USPSP1) filed on Jun. 4, 2020 and U.S. Provisional Patent Application No. 63/061,929 (JNJBIO-6368USPSP1) filed on Aug. 6, 2020, which are incorporated by reference as if fully set forth.

FIELD OF INVENTION

The present invention is related to signal processing, artificial intelligence, and machine learning. More particularly, the present invention is related to a system and method for reducing noise of intracardiac electrocardiograms using an autoencoder and utilizing and refining intracardiac and body surface electrocardiograms using one or more deep learning training loss functions.

BACKGROUND

Treatments for cardiac conditions, such as cardiac arrhythmia, often require heart mapping (i.e., mapping cardiac tissue, chambers, veins, arteries and/or pathways, which is also known as cardiac mapping). Electrocardiograms or electrocardiographs (ECGs) are examples of heart mappings. ECGs are generated from electrical signals from a heart that describe heart activity. ECGs are utilized during cardiac procedures to identify potential origination locations of cardiac conditions.

An autoencoder may be utilized to refine the electrical signals of the heart through encoding and decoding operations. The refined electrical signals of the heart may then be used to generate the ECGs. The autoencoder utilizes artificial intelligence and machine learning to build and train the encoding and decoding operations therein. For example, a denoising autoencoder trains the autoencoder to discover more robust features/representations within the electrical signals and prevents the autoencoder from learning a particular identity of the electrical signals. When trying to extract or learn important features/representations during autoencoder training, present mean square error (MSE) functions and/or other regression loss functions fail to emphasize zones or events of clinical importance (e.g., potential origination locations of cardiac conditions).

SUMMARY

According to an embodiment, a method is provided. The method includes receiving raw signal data including signal noise and encoding, by a denoised autoencoder, the raw signal data. The encoding includes performing a denoising autoencoder operation on the raw signal data to produce a latent representation. The method also includes decoding, by the denoised autoencoder, the latent representation to produce clean signal data reconstructed without the signal noise.

According to an embodiment, another method is provided. The method is implemented by a training algorithm executed by a processor coupled to a memory. The training algorithm applies a first filter to a signal to emphasize activity within the signal and to produce a first modified signal. The training algorithm applies a rectifier and a second filter to the first modified signal to smooth areas of the first modified signal with clinical importance and to produce a second modified signal. The training algorithm automatically detects high frequency energy zones of the second modified signal using an energy threshold to produce a weights vector.

According to one or more embodiments, the method embodiments above can be implemented as an apparatus, a system, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 3 illustrates a graphical depiction of an artificial intelligence system according to one or more embodiments;

FIG. 12 illustrates a block diagram of a method according to one or more embodiments;

DETAILED DESCRIPTION

Figure 1:
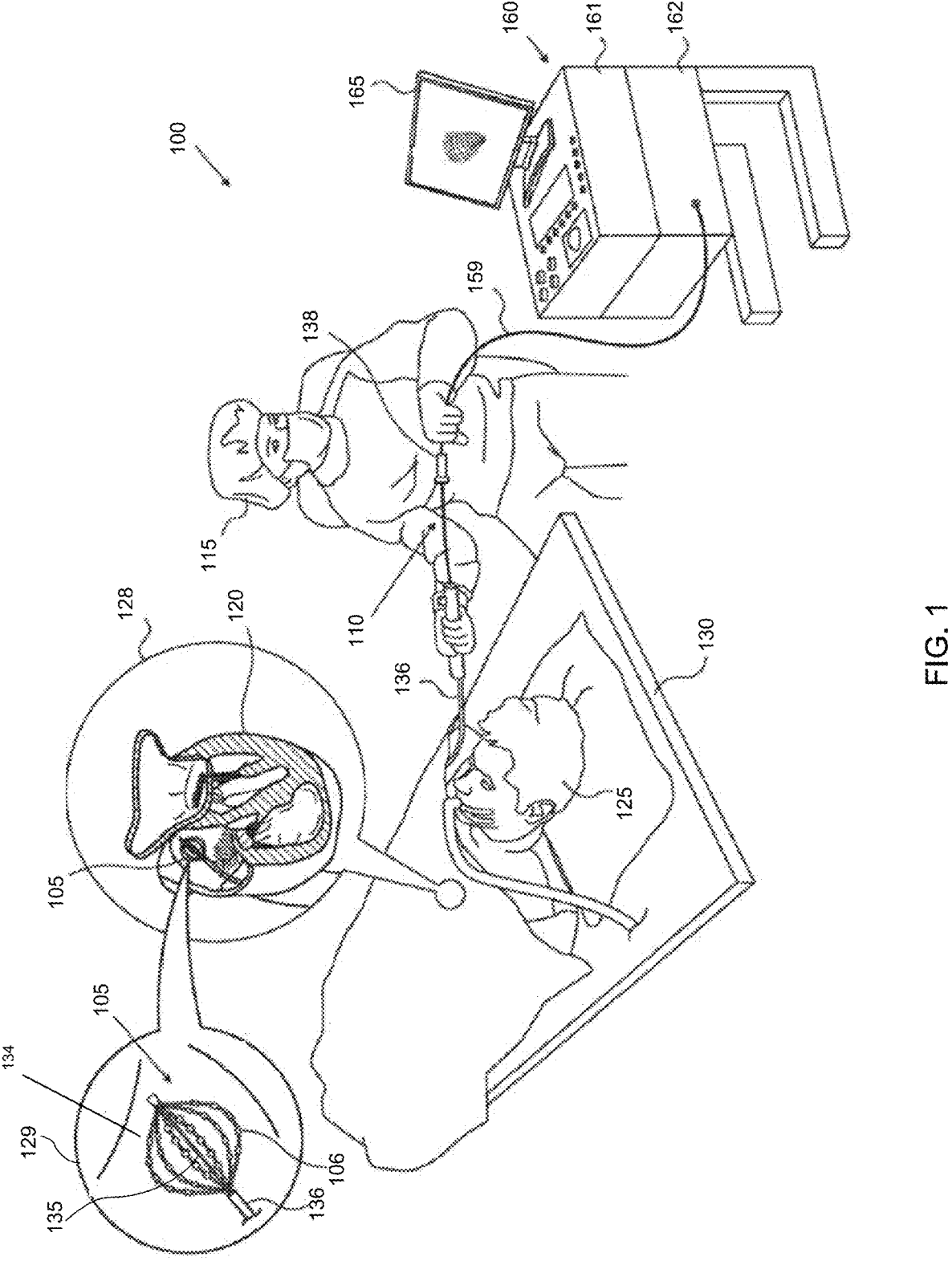
FIG. 1 illustrates a diagram of an exemplary system in which one or more features of the disclosure subject matter can be implemented according to one or more embodiments.

Disclosed herein is a system for utilizing and refining intracardiac and body surface electrocardiograms using one or more deep learning training loss functions (i.e., a type of an artificial intelligence and machine learning operation), which is generally referred to herein as a training algorithm. The training algorithm of the system for utilizing and refining intracardiac and body surface electrocardiograms is a processor executable code or software that is necessarily rooted in process operations by, and in processing hardware of, medical device equipment to provide improved ECGs and intracardiac ECGs for treating cardiac conditions. According to an embodiment, the training algorithm provides a specific training method for the medical device equipment and autoencoders therein. This specific training method involves a multi-step data manipulation of electrical signals of a heart that emphasize zones or events of clinical importance (e.g., potential origination locations of cardiac conditions) within the electrical signals.

In this regard and in operation, the training algorithm of the system for utilizing and refining intracardiac and body surface electrocardiogram receives a signal. This signal can be an electrical signal from a heart that describes heart activity. The signal can be stored within the medical device equipment or provided to the medical device equipment. The training algorithm processes the signal to clean it. In this regard, the training algorithm applies a first filter to a signal to emphasize activity within the signal and to produce a first modified signal, applies a rectifier and a second filter to the first modified signal to smooth areas of the first modified signal with clinical importance and to produce a second modified signal, and automatically detects high frequency energy zones of the second modified signal using an energy threshold to produce a weights vector. (e.g., based on the weights vector, a weighted MSE loss function is defined and used to train a denoising autoencoder). The training algorithm further builds a training dataset including at least the weights vector and trains an autoencoder (e.g., any autoencoder type) using the training dataset. In turn, the autoencoder can generate improved electrocardiograms from one or more output intracardiac signals outputted by the autoencoder.

The benefits of the system for utilizing and refining intracardiac and body surface electrocardiogram (and training algorithm therein) include reducing an overall training of the autoencoder by a factor of ten (10) and increasing the accuracy and consistency of reconstruction/denoising of the signals of the trained autoencoder. In addition, the technical effects and benefits of the system further enable the generation of the improved ECGs and intracardiac ECGs to physicians (such as during cardiac procedures) who use the improved ECGs and intracardiac ECGs to study heart activity to identify potential origination locations of cardiac conditions.

FIG. 1 is a diagram of an exemplary system 100 (e.g., medical device equipment) in which one or more features of the disclosure subject matter can be implemented. All or parts of system 100 may be used to collect information for a training dataset and/or all or parts of system 100 may be used to implement the training algorithm to train the autoencoder (e.g., a trained model). The autoencoder (e.g., an artificial intelligence and machine learning autoencoder) is a processor executable code or software that is necessarily rooted in process operations by, and in processing hardware of, medical device equipment to provide improved ECGs and intracardiac ECGs for treating cardiac conditions.

According to one or more embodiments, the autoencoder can receive input intracardiac signals (e.g., the electrical signals of the heart that include signal interference, signal artifacts, and signal noise). The intracardiac signals can be, in real time, recorded and processed by a monitoring and processing apparatus (e.g., a catheter with the autoencoder therein) and/or recorded and transmitted by the monitoring and processing apparatus to a computing device with the autoencoder therein. The autoencoder can encode the input intracardiac signals utilizing an intracardiac dataset (e.g., predetermined and approved electrical signals of the heart that are free from signal interference, signal artifacts, and signal noise). This encoding by the autoencoder produces a latent representation from the input intracardiac signals. The autoencoder can further decode the latent representation to produce output intracardiac signals. The output intracardiac signals are the input intracardiac signals reconstructed without the signal interference, signal artifacts, and signal noise. The improved ECGs and intracardiac ECGs for treating cardiac conditions can then be generated from the output intracardiac signals.

The autoencoder encodes the raw signal data by performing a denoising autoencoder operation (e.g., passing the raw signal data through a deep neural network, such as a convolutional neural network (CNN) architecture) to reduce a dimensionality of the raw signal data and retain only important information therein (e.g. the denoising autoencoder operation cleans the raw signal data). In this encoding stage, the autoencoder produces a latent representation, which has the reduced dimensionality and the important information, from the raw signal data.

The autoencoder further decodes the latent representation to produce, as an output, a reconstruction of a clean version of the raw signal data. That is, in this decoding stage, the autoencoder reconstructs a clean signal data from the latent representation. More particularly, the clean signal data (i.e., the output of the decoding stage) includes the input intracardiac signals reconstructed without the signal noise. In turn, the autoencoder learns the clean signal data to further denoise subsequent raw intracardiac signals and generate corresponding final outputs (e.g., the improved ECGs).

The technical effects and benefits of the autoencoder include producing the output, in real time, which further enable the generation of the improved ECGs to physicians (such as during cardiac procedures) who use the improved ECGs to study heart activity to identify potential origination locations of cardiac conditions. Note that the improved ECGs are not obscured by the signal noise of the raw signal data, as these concerns have been removed during encoding. Further, the technical effects and benefits of the autoencoder include producing the improved ECGs with an increased accuracy (as the signal noise is removed) so that ventricle and atria origination locations can be separately provided in real time cases.

FIG. 1 is a diagram of an exemplary system 100 (e.g., medical device equipment) in which one or more features of the disclosure subject matter can be implemented. All or parts of system 100 may be used to collect information for learning clean signal data (e.g., training an autoencoder) and/or all or parts of system 100 may be used to produce improved ECGs (e.g., implement a trained autoencoder to denoise subsequent raw data inputs) described herein.

The system 100 may include components, such as a catheter 105, that are configured to damage tissue areas of an intra-body organ. The catheter 105 may also be further configured to obtain biometric data including the electrical signals of the heart (e.g., the intracardiac signals). Although the catheter 105 is shown to be a point catheter, it will be understood that a catheter of any shape that includes one or more elements (e.g., electrodes) may be used to implement the embodiments disclosed herein.

The system 100 includes a probe 110, having shafts that may be navigated by a physician or a medical professional 115 into a body part, such as a heart 120, of a patient 125 lying on a bed (or a table) 130. According to embodiments, multiple probes may be provided; however, for purposes of conciseness, a single probe 110 is described herein. Yet, it is understood that the probe 110 may represent multiple probes.

The exemplary system 100 can be utilized to detect, diagnose, and treat cardiac conditions (e.g., using the intra-cardiac signals). Cardiac conditions, such as cardiac arrhyth-mias (atrial fibrillation in particular), persist as common and dangerous medical ailments, especially in the aging popu-lation. In patients (e.g., the patient 125) with normal sinus rhythm, the heart (e.g., the heart 120), which includes atrial, ventricular, and excitatory conduction tissue, is electrically excited to beat in a synchronous, patterned fashion (note that this electrical excitement can be detected as intracardiac signals).

In patients (e.g., the patient 125) with cardiac arrhyth-mias, abnormal regions of cardiac tissue do not follow the synchronous beating cycle associated with normally con-ductive tissue as in patients with normal sinus rhythm. Instead, the abnormal regions of cardiac tissue aberrantly conduct to adjacent tissue, thereby disrupting the cardiac cycle into an asynchronous cardiac rhythm (note that this asynchronous cardiac rhythm can also be detected as intra-cardiac signals). Such abnormal conduction has been pre-viously known to occur at various regions of the heart (e.g., the heart 120), for example, in the region of the sino-atrial (SA) node, along the conduction pathways of the atrioven-tricular (AV) node, or in the cardiac muscle tissue forming the walls of the ventricular and atrial cardiac chambers.

Further, cardiac arrhythmias, including atrial arrhythmias, may be of a multiwavelet reentrant type, characterized by multiple asynchronous loops of electrical impulses that are scattered about the atrial chamber and are often self-propa-gating (e.g., another example of intracardiac signals). Alter-natively, or in addition to the multiwavelet reentrant type, cardiac arrhythmias may also have a focal origin, such as when an isolated region of tissue in an atrium fires autono-mously in a rapid, repetitive fashion (e.g., another example of the intracardiac signals). Ventricular tachycardia (V-tach or VT) is a tachycardia, or fast heart rhythm that originates in one of the ventricles of the heart. This is a potentially life-threatening arrhythmia because it may lead to ventricu-lar fibrillation and sudden death.

One type of arrhythmia, atrial fibrillation, occurs when the normal electrical impulses (e.g., another example of the intracardiac signals) generated by the sinoatrial node are overwhelmed by disorganized electrical impulses (e.g., the signal interference) that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. The first line of treatment for AF is medication that either slows the heart rate or reverts the heart rhythm back to normal. Additionally, per-sons with AF are often given anticoagulants to protect them from the risk of stroke. The use of such anticoagulants comes with its own risk of internal bleeding. In some patients, medication is not sufficient, and their AF is deemed to be drug-refractory, i.e., untreatable with standard phar-macological interventions. Synchronized electrical cardioversion may also be used to convert AF to a normal heart rhythm. Alternatively, AF patients are treated by catheter ablation.

A catheter ablation-based treatment may include mapping the electrical properties of heart tissue, especially the endo-cardium and the heart volume, and selectively ablating cardiac tissue by application of energy. Cardiac mapping (e.g., heart mapping), for example, includes creating a map of electrical potentials (e.g., a voltage map) of the wave propagation along the heart tissue or a map of arrival times (e.g., a local time activation (LAT) map) to various tissue located points. Cardiac mapping may be used for detecting local heart tissue dysfunction. Ablations, such as those based on cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step proce-dure—mapping followed by ablation—electrical activity at points within the heart is typically sensed and measured by advancing a catheter (e.g., the catheter 105) containing one or more electrical sensors (e.g., the at least one ablation electrode 134 of the catheter 105) into the heart (e.g., the heart 120), and acquiring data at a multiplicity of points. This data (e.g., biometric data including the intracardiac signals) is then utilized to select the endocardial target areas, at which ablation is to be performed. Note that, due to the use of the autoencoder trained by the training algorithm (e.g., employed by the exemplary system 100), this data is more accurate and better able to support selecting the endocardial target areas for ablation than the underlying electrical signals of the ECGs that include signal interfer-ence, signal artifacts, and signal noise. The signal interfer-ence, the signal artifacts, and the signal noise can be collectively referred to herein as artifacts.

Cardiac ablation and other cardiac electrophysiological procedures have become increasingly complex as clinicians treat challenging conditions such as atrial fibrillation and ventricular tachycardia. The treatment of complex arrhyth-mias can now rely on the use of three-dimensional (3D) mapping systems in order to reconstruct the anatomy of the heart chamber of interest. In this regard, the autoencoder trained by the training algorithm (e.g., employed by the exemplary system 100) herein provides the underlying out-put signals so that improved 3D maps and/or ECGs for treating cardiac conditions can be generated.

For example, cardiologists rely upon software, such as the Complex Fractionated Atrial Electrograms (CFAE) module of the CARTO® 3 3D mapping system, produced by Bio-sense Webster, Inc. (Diamond Bar, Calif.), to generate and analyze intracardiac electrograms (EGM). The autoencoder trained by the training algorithm (e.g., employed by the exemplary system 100) enhances this software to generate and analyze improved intracardiac electrograms (EGM) so that the ablation points can be determined for treatment of a broad range of cardiac conditions, including atypical atrial flutter and ventricular tachycardia.

The improved 3D maps supported by the autoencoder trained by the training algorithm (e.g., employed by the exemplary system 100) can provide multiple pieces of information regarding the electrophysiological properties of the tissue that represent the anatomical and functional sub-strate of these challenging arrhythmias.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes.

Abnormal tissue is generally characterized by low-voltage EGMs. However, initial clinical experience in endo-epicardial mapping indicates that areas of low-voltage are not always present as the sole arrhythmogenic mechanism in such patients. In fact, areas of low or medium voltage may exhibit EGM fragmentation and prolonged activities during sinus rhythm, which corresponds to the critical isthmus identified during sustained and organized ventricular arrhythmias, e.g., applies only to non-tolerated ventricular tachycardias. Moreover, in many cases, EGM fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping may be able to localize the arrhythmogenic substrate on the endocardial and/or epicardial layer of the right/left ventricle, which may vary in distribution according to the extension of the main disease.

The substrate linked to these cardiac conditions is related to the presence of fragmented and prolonged EGMs in the endocardial and/or epicardial layers of the ventricular chambers (right and left). The 3D mapping system, such as CARTO® 3, is able to localize the potential arrhythmogenic substrate of the cardiomyopathy in terms of abnormal EGM detection.

Electrode catheters (e.g., the catheter 105) are use in medical practice. Electrode catheters are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having at least one electrode at its distal end, into a heart chamber. A reference electrode is provided, generally taped to the skin of the patient or by means of a second catheter that is positioned in or near the heart. Radio frequency (RF) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees Celsius, a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs, and the catheter must be removed from the body and the tip electrode cleaned.

Treatments for cardiac conditions such as cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in the heart chamber. Such locating may be done via an electrophysiological investigation during which electrical potentials are detected spatially resolved with a mapping catheter introduced into the heart chamber. This electrophysiological investigation, the so-called electro-anatomical mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time. In this case, the training algorithm and/or the autoencoder trained by the training algorithm can be directly stored and executed by the catheter 105.

Mapping of cardiac areas such as cardiac regions, tissue, veins, arteries and/or electrical pathways of the heart (e.g., 120) may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

Cardiac mapping may be implemented using one or more techniques. As an example of a first technique, cardiac mapping may be implemented by sensing an electrical property of heart tissue, for example, LAT, as a function of the precise location within the heart. The corresponding data may be acquired with one or more catheters that are advanced into the heart using catheters that have electrical and location sensors in their distal tips. As specific examples, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Returning to FIG. 1, to implement the noted cardiac mapping, the medical professional 115 may insert a shaft through a sheath 136, while manipulating a distal end of the shaft using a manipulator 138 near the proximal end of the catheter 105 and/or deflection from the sheath 136. As shown in an inset 140, the catheter 105 may be fitted at the distal end of the shaft. The catheter 105 may be inserted through the sheath 136 in a collapsed state and may be then expanded within the heart 120. The catheter 105 may include at least one ablation electrode 134 and a catheter needle, as further disclosed herein.

According to embodiments, the catheter 105 may be configured to ablate tissue areas of a cardiac chamber of the heart 120. Inset 150 shows the catheter 105 in an enlarged view, inside a cardiac chamber of the heart 120. As shown, the catheter 105 may include the at least one ablation electrode 134 coupled onto the body of the catheter. According to other embodiments, multiple elements may be connected via splines that form the shape of the catheter 105. One or more other elements (not shown) may be provided and may be any elements configured to ablate or to obtain biometric data and may be electrodes, transducers, or one or more other elements.

According to embodiments disclosed herein, the ablation electrodes, such as the at least one ablation electrode 134, may be configured to provide energy to tissue areas of an intra-body organ such as heart 120. The energy may be thermal energy and may cause damage to the tissue area starting from the surface of the tissue area and extending into the thickness of the tissue area.

According to embodiments disclosed herein, biometric data may include one or more of LATs, electrical activity, topology, bipolar mapping, dominant frequency, impedance, or the like. The LAT may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. For instance, the autoencoder can detect a noise type and/or quality of the electrical and compare the noise type and/or quality to the one or more thresholds. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 110 and the catheter 105 may be connected to a console 160. The console 160 may include a computing device 161, which employs the training algorithm and/or the autoencoder trained by the training algorithm as described herein. According to an embodiment, the console 160 and/or the computing device 161 include at least a processor and a memory, where the processor executes computer instructions with respect the training algorithm and/or the autoencoder and the memory stores the instructions for execution by the processor.

The computing device 161 can be any computing device including software and/or hardware, such as a general-purpose computer, with suitable front end and interface circuits 162 for transmitting and receiving signals to and from the catheter 105, as well as for controlling the other components of system 100. The computing device 161 may include real-time noise reduction circuitry typically configured as a field programmable gate array (FPGA), followed by an analog-to-digital (A/D) electrocardiograph or electromyogram (EMG) signal conversion integrated circuit. The computing device 161 may pass the signal from an A/D ECG or EMG circuit to another processor and/or can be programmed to perform one or more functions disclosed herein.

For example, the one or more functions include applying a first filter to a signal to emphasize activity within a signal and to produce a first modified signal, apply a rectifier and a second filter to the first modified signal to smooth areas of the first modified signal with clinical importance and to produce a second modified signal, and automatically detect high frequency energy zones of the second modified signal using an energy threshold to produce a weights vector that is used to build a training dataset. Further, the one or more functions include receiving input intracardiac signals, encoding the input intracardiac signals utilizing an intracardiac dataset to produce a latent representation, and decoding the latent representation to produce output intracardiac signals. The front end and interface circuits 162 include input/output (I/O) communication interfaces that enables the console 160 to receive signals from and/or transfer signals to the at least one ablation electrode 134.

In some embodiments, the computing device 161 may be further configured to receive biometric data, such as electrical activity, and determine if a given tissue area conducts electricity. According to an embodiment, the computing device 161 may be external to the console 160 and may be located, for example, in the catheter, in an external device, in a mobile device, in a cloud-based device, or may be a standalone processor.

As noted above, the computing device 161 may include a general-purpose computer, which may be programmed in software to carry out the functions of the training algorithm and/or the autoencoder described herein. The software may be downloaded to the general-purpose computer in electronic form, over a network, for example, or it may, alternatively or additionally, be provided and/or stored on non-transitory tangible media, such as magnetic, optical, or electronic memory (e.g., any suitable volatile and/or non-volatile memory, such as random-access memory or a hard disk drive). The example configuration shown in FIG. 1 may be modified to implement the embodiments disclosed herein. The disclosed embodiments may similarly be applied using other system components and settings. Additionally, system 100 may include additional components, such as elements for sensing electrical activity, wired or wireless connectors, processing and display devices, or the like.

According to an embodiment, a display 165 is connected to the computing device 161. During a procedure, the computing device 161 may facilitate the presentation of a body part rendering to the medical professional 115 on a display 165, and store data representing the body part rendering in a memory. In some embodiments, the medical professional 115 may be able to manipulate the body part rendering using one or more input devices such as a touch pad, a mouse, a keyboard, a gesture recognition apparatus, or the like. For example, an input device may be used to change a position of the catheter 105, such that rendering is updated. In alternative embodiments, the display 165 may include a touchscreen that can be configured to accept inputs from the medical professional 115, in addition to presenting the body part rendering. Note that the display 165 may be located at a same location or a remote location such as a separate hospital or in separate healthcare provider networks. Additionally, the system 100 may be part of a surgical system that is configured to obtain anatomical and electrical measurements of a patient's organ, such as the heart 120, and performing a cardiac ablation procedure. An example of such a surgical system is the Carto® system sold by Biosense Webster.

The console 160 may be connected, by a cable, to body surface electrodes, which may include adhesive skin patches that are affixed to the patient 125. The processor, in conjunction with a current tracking module, may determine position coordinates of the catheter 105 inside the body part (e.g., the heart 120) of the patient 125. The position coordinates may be based on impedances or electromagnetic fields measured between the body surface electrodes and the electrode or other electromagnetic components (e.g., the at least one ablation electrode 134) of the catheter 105. Additionally, or alternatively, location pads may be located on a surface of bed 130 and may be separate from the bed 130.

The system 100 may also, and optionally, obtain biometric data such as anatomical measurements of the heart 120 using ultrasound, computed tomography (CT), magnetic resonance imaging (MRI) or other medical imaging techniques known in the art. The system 100 may obtain ECGs or electrical measurements using catheters or other sensors that measure electrical properties of the heart 120. The biometric data including anatomical and electrical measurements may then be stored in a non-transitory tangible media of the console 160. The biometric data may be transmitted to the computing device 161 from the non-transitory tangible media. Alternatively, or in addition, the biometric data may be transmitted to a server, which may be local or remote, using a network as further described herein.

According to one or more embodiments, catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart 120.

Electrical activity at a point in the heart 120 may be typically measured by advancing the catheter 105 containing an electrical sensor at or near its distal tip (e.g., the at least one ablation electrode 134) to that point in the heart 120, contacting the tissue with the sensor and acquiring data at that point. One drawback with mapping a cardiac chamber using the catheter 105 containing only a single, distal tip electrode is the long period of time required to accumulate data on a point-by-point basis over the requisite number of points required for a detailed map of the chamber as a whole. Accordingly, multiple-electrode catheters, as shown by balloon catheter 135, have been developed to simultaneously measure electrical activity at multiple points in the heart chamber.

Multiple-electrode catheters may be implemented using any applicable shape such as a linear catheter with multiple electrodes, a balloon catheter 135 including electrodes dispersed on multiple spines that shape the balloon, a lasso or loop catheter with multiple electrodes, or any other applicable shape. Linear catheter may be fully or partially elastic such that it can twist, bend, and or otherwise change its shape based on received signal and/or based on application of an external force (e.g., cardiac tissue) on the linear catheter. The balloon catheter 135 may be designed such that when deployed into a patient's body, its electrodes may be held in intimate contact against an endocardial surface. As an example, a balloon catheter 135 may be inserted into a lumen, such as a pulmonary vein (PV). The balloon catheter 135 may be inserted into the PV in a deflated state such that the balloon catheter does not occupy its maximum volume while being inserted into the PV. The balloon catheter 135 may expand while inside the PV such those electrodes on the balloon catheter 135 are in contact with an entire circular section of the PV. Such contact with an entire circular section of the PV, or any other lumen, may enable efficient mapping and/or ablation.

According to an example, a multi-electrode catheter may be advanced into a chamber of the heart 120. Anteroposterior (AP) and lateral fluorograms may be obtained to establish the position and orientation of each of the electrodes. EGMs may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial EGMs are recorded, the catheter may be repositioned, and fluorograms and EGMs may be recorded again. An electrical map may then be constructed from iterations of the process above.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an electrophysiological cardiac mapping system and technique based on a non-contact and non-expanded multi-electrode catheter may be implemented. EGMs may be obtained with catheters having multiple electrodes (e.g., between 42 to 122 electrodes). According to this implementation, knowledge of the relative geometry of the probe and the endocardium may be obtained such as by an independent imaging modality such as transesophageal echocardiography. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart 120; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

According to another example, a technique and apparatus for mapping the electrical potential distribution of a heart chamber may be implemented. An intra-cardiac multi-electrode mapping catheter assembly may be inserted into a patient's heart 120. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

According to another example, a heart mapping catheter assembly may include an electrode array defining a number of electrode sites. The mapping catheter assembly may also include a lumen to accept a reference catheter having a distal tip electrode assembly which may be used to probe the heart wall. The mapping catheter may include a braid of insulated wires (e.g., having 24 to 64 wires in the braid), and each of the wires may be used to form electrode sites. The catheter may be readily positionable in the heart 120 to be used to acquire electrical activity information from a first set of non-contact electrode sites and/or a second set of in-contact electrode sites.

According to another example, another catheter for mapping electrophysiological activity within the heart may be implemented. The catheter body may include a distal tip which is adapted for delivery of a stimulating pulse for pacing the heart or an ablative electrode for ablating tissue in contact with the tip. The catheter may further include at least one pair of orthogonal electrodes to generate a difference signal indicative of the local cardiac electrical activity adjacent the orthogonal electrodes.

According to another example, a process for measuring electrophysiological data in a heart chamber may be implemented. The method may include, in part, positioning a set of active and passive electrodes into the heart 120, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to another example, cardiac mapping may be implemented using one or more ultrasound transducers. The ultrasound transducers may be inserted into a patient's heart 120 and may collect a plurality of ultrasound slices (e.g., two dimensional or three-dimensional slices) at various locations and orientations within the heart 120. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart 120) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart 120). The biometric data may be associated with the determined position of the catheter such that a rendering of the patient's body part (e.g., heart 120) may be displayed and may show the biometric data overlaid on a shape of the body.

Figure 2:
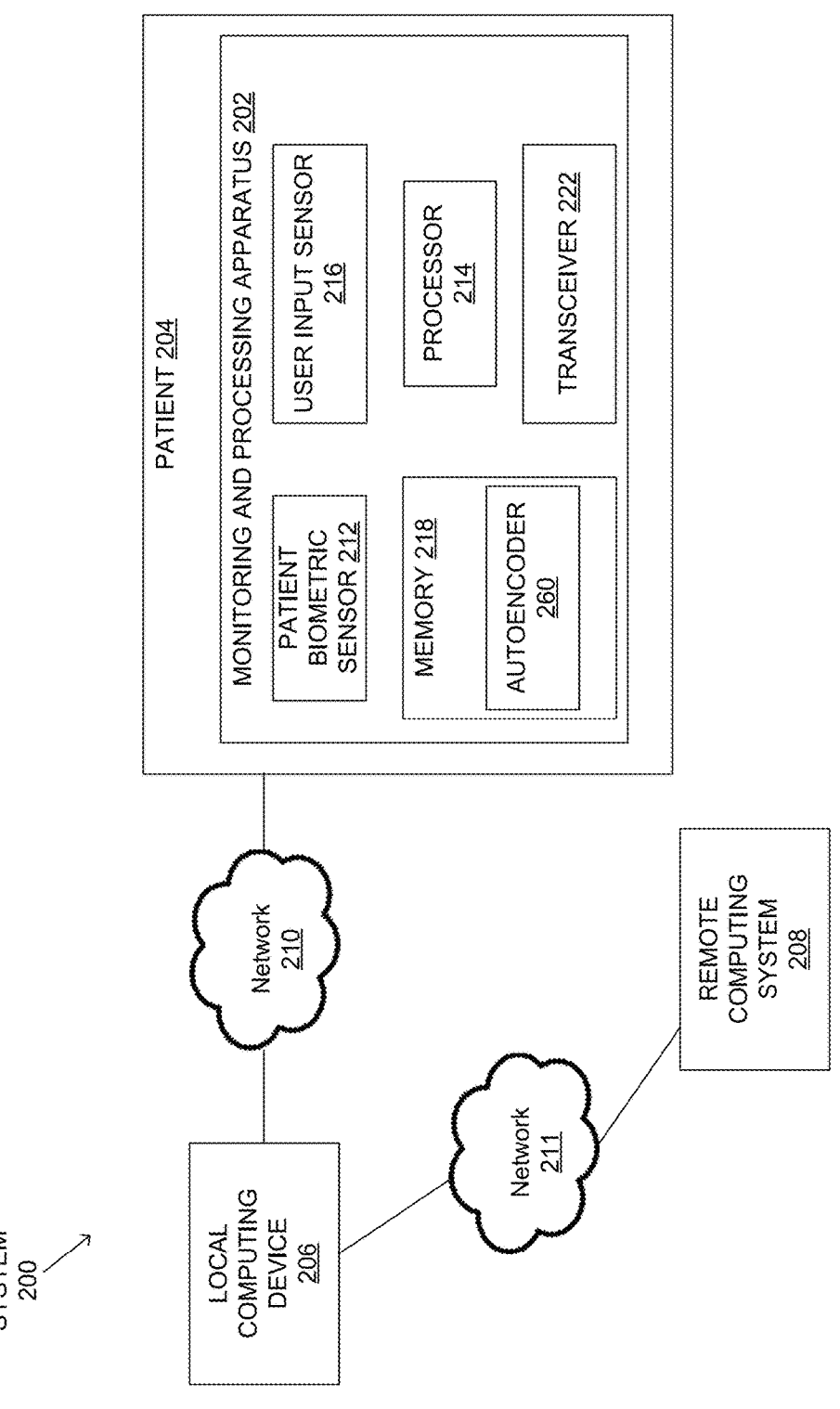
FIG. 2 illustrates a block diagram of an example system for remotely monitoring and communicating patient biometrics according to one or more embodiments.

Turning now to FIG. 2, a block diagram of an example system 200 for remotely monitoring and communicating biometric data (i.e., patient biometrics, patient data, or patient biometric data) is illustrated. In the example illustrated in FIG. 2, the system 200 includes a monitoring and processing apparatus 202 (i.e., a patient data monitoring and processing apparatus) associated with a patient 204, a local computing device 206, a remote computing system 208, a first network 210, and a second network 211. In accordance with one or more embodiments, the monitoring and processing apparatus 202 can be an example of the catheter 105 of FIG. 1, the patient 204 can be an example of the patient 125 of FIG. 1, and the local computing device 206 can be an example of the console 160 of FIG. 1.

The monitoring and processing apparatus 202 includes a patient biometric sensor 212, a processor 214, a user input (UI) sensor 216, a memory 218, and a transmitter-receiver (i.e., transceiver) 222. In operation, the monitoring and processing apparatus 202 acquires biometric data of the patient 204 (e.g., electrical signals, blood pressure, temperature, blood glucose level or other biometric data) and/or receives at least a portion of the biometric data representing any acquired patient biometrics and additional information associated with any acquired patient biometrics from the one or more other patient biometric monitoring and processing apparatuses. The additional information may be, for example, diagnosis information and/or additional information obtained from an additional device such as a wearable device.

The monitoring and processing apparatus 202 may employ the training algorithm described herein to apply a first filter to a signal to emphasize activity within a signal and to produce a first modified signal, apply a rectifier and a second filter to the first modified signal to smooth areas of the first modified signal with clinical importance and to produce a second modified signal, and automatically detect high frequency energy zones of the second modified signal using an energy threshold to produce a weights vector, such that high weights corresponds to clinical importance areas and low weights are associated with other areas.

The monitoring and processing apparatus 202 may employ the autoencoder 260 described herein to process data, including the acquired biometric data as well as any biometric data received from the one or more other patient biometric monitoring and processing apparatuses. For example, when processing data in this regard, the autoencoder 260 includes a neural network that is used to learn latent representations (or data codings) in an unsupervised manner from the biometric data. Further, the autoencoder learns to detect specific data by training (using the training algorithm) the neural network to ignore signal interference, signal artifacts, and signal noise by considering clean datasets, without being pre-programmed with specific rules.

The monitoring and processing apparatus 202 may continually or periodically monitor, store, process, and communicate, via network 210, any number of various patient biometrics (e.g., the acquired biometric data). As described herein, examples of patient biometrics include electrical signals (e.g., ECG signals and brain biometrics), blood pressure data, blood glucose data, and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

The patient biometric sensor 212 may include, for example, one or more transducers configured to convert one or more environmental conditions into an electrical signal, such that different types of biometric data are acquired. For example, the patient biometric sensor 212 may include one or more of an electrode configured to acquire electrical signals (e.g., heart signals, brain signals, or other bioelectrical signals), a temperature sensor (e.g., thermocouple), a blood pressure sensor, a blood glucose sensor, a blood oxygen sensor, a pH sensor, an accelerometer, and a microphone.

As described in more detail herein, the monitoring and processing apparatus 202 may be an ECG monitor for monitoring ECG signals of a heart (e.g., the heart 120 of FIG. 1). In this regard, the patient biometric sensor 212 of the ECG monitor may include one or more electrodes (e.g., electrodes of the catheter 105 of FIG. 1) for acquiring ECG signals. The ECG signals may be used for treatment of various cardiovascular diseases.

In another example, the monitoring and processing apparatus 202 may be a continuous glucose monitor (CGM) for continuously monitoring blood glucose levels of a patient on a continual basis for treatment of various diseases, such as type I and type II diabetes. In this regard, the patient biometric sensor 212 of the CGM may include a subcutaneously disposed electrode (e.g., electrodes of the catheter 105 of FIG. 1), which may monitor blood glucose levels from interstitial fluid of the patient. The CGM may be, for example, a component of a closed-loop system in which the blood glucose data is sent to an insulin pump for calculated delivery of insulin without user intervention.

The processor 214 may be configured to receive, process, and manage, biometric data acquired by the patient biometric sensor 212, and communicate the biometric data to the memory 218 for storage and/or across the network 210 via the transceiver 222. Data from one or more other monitoring and processing apparatus 202 may also be received by the processor 214 through the transceiver 222, as described in more detail herein. Also, as described in more detail herein, the processor 214 may be configured to respond selectively to different tapping patterns (e.g., a single tap or a double tap) received from the UI sensor 216 (e.g., a capacitive sensor therein), such that different tasks of a patch (e.g., acquisition, storing, or transmission of data) may be activated based on the detected pattern. In some embodiments, the processor 214 can generate audible feedback with respect to detecting a gesture.

The UI sensor 216 includes, for example, a piezoelectric sensor or a capacitive sensor configured to receive a user input, such as a tapping or touching. For example, UI sensor 216 may be controlled to implement a capacitive coupling, in response to tapping or touching a surface of the monitoring and processing apparatus 202 by the patient 204. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 218 is any non-transitory tangible media, such as magnetic, optical, or electronic memory (e.g., any suitable volatile and/or non-volatile memory, such as random-access memory or a hard disk drive). According to one or more embodiments, the memory 218 stores processor executable code, software, or instructions of the training algorithm and of the autoencoder.

The transceiver 222 may include a separate transmitter and a separate receiver. Alternatively, the transceiver 222 may include a transmitter and receiver integrated into a single device.

According to an embodiment, the monitoring and processing apparatus 202 may be an apparatus that is internal to a body of the patient 204 (e.g., subcutaneously implantable). The monitoring and processing apparatus 202 may be inserted into the patient 204 via any applicable manner including orally injecting, surgical insertion via a vein or artery, an endoscopic procedure, or a lap aroscopic procedure.

According to an embodiment, the monitoring and processing apparatus 202 may be an apparatus that is external to the patient 204. For example, as described in more detail herein, the monitoring and processing apparatus 202 may include an attachable patch (e.g., that attaches to a patient's skin). The monitoring and processing apparatus 202 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an embodiment, a monitoring and processing apparatus 202 may include both components that are internal to the patient and components that are external to the patient.

While a single monitoring and processing apparatus 202 is shown in FIG. 2, example systems may include a plurality of patient biometric monitoring and processing apparatuses. For instance, the monitoring and processing apparatus 202 may be in communication with one or more other patient biometric monitoring and processing apparatuses. Additionally, or alternatively, the one or more other patient biometric monitoring and processing apparatus may be in communication with the network 210 and other components of the system 200.

The local computing device 206 and/or the remote computing system 208, along with the monitoring and processing apparatus 202, can be any combination of software and/or hardware that individually or collectively store, execute, and implement the training algorithm, the autoencoder, and functions thereof. Further, the local computing device 206 and/or the remote computing system 208, along with the monitoring and processing apparatus 202, can be an electronic, computer framework including and/or employing any number and combination of computing device and networks utilizing various communication technologies, as described herein. The local computing device 206 and/or the remote computing system 208, along with the monitoring and processing apparatus 202, can be easily scalable, extensible, and modular, with the ability to change to different services or reconfigure some features independently of others.

According to an embodiment, the local computing device 206 and the remote computing system 208, along with the monitoring and processing apparatus 202, include at least a processor and a memory, where the processor executes computer instructions with respect the training algorithm and the autoencoder and the memory stores these computer instructions for execution by the processor.

The local computing device 206 of system 200 is in communication with the monitoring and processing apparatus 202 and may be configured to act as a gateway to the remote computing system 208 through the second network 211. The local computing device 206 may be, for example, a, smart phone, smartwatch, tablet or other portable smart device configured to communicate with other devices via network 211. Alternatively, the local computing device 206 may be a stationary or standalone device, such as a stationary base station including, for example, modem and/or router capability, a desktop or laptop computer using an executable program to communicate information between the processing apparatus 202 and the remote computing system 208 via the PC's radio module, or a USB dongle. Biometric data may be communicated between the local computing device 206 and the monitoring and processing apparatus 202 using a short-range wireless technology standard (e.g., Bluetooth, Wi-Fi, ZigBee, Z-wave and other short-range wireless standards) via the short-range wireless network 210, such as a local area network (LAN) (e.g., a personal area network (PAN)). In some embodiments, the local computing device 206 may also be configured to display the acquired patient electrical signals and information associated with the acquired patient electrical signals, as described in more detail herein.

In some embodiments, the remote computing system 208 may be configured to receive at least one of the monitored patient biometrics and information associated with the monitored patient via network 211, which is a long-range network. For example, if the local computing device 206 is a mobile phone, network 211 may be a wireless cellular network, and information may be communicated between the local computing device 206 and the remote computing system 208 via a wireless technology standard, such as any of the wireless technologies mentioned above. As described in more detail herein, the remote computing system 208 may be configured to provide (e.g., visually display and/or aurally provide) the at least one of the patient biometrics and the associated information to a medical professional, a physician, a healthcare professional, or the like.

In FIG. 2, the network 210 is an example of a short-range network (e.g., local area network (LAN), or personal area network (PAN)). Information may be sent, via short-range network 210, between the monitoring and processing apparatus 202 and the local computing device 206 using any one of various short-range wireless communication protocols, such as Bluetooth, Wi-Fi, Zigbee, Z-Wave, near field communications (NFC), ultraband, Zigbee, or infrared (IR).

The network 211 may be a wired network, a wireless network or include one or more wired and wireless networks, such as an intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information may be sent, via the network 211 using any one of various long-range wireless communication protocols (e.g., TCP/IP, HTTP, 3G, 4G/LTE, or 5G/New Radio). Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology. Additionally, several networks may work alone or in communication with each other to facilitate communication in the network 211. In some instances, the remote computing system 208 may be implemented as a physical server on the network 211. In other instances, the remote computing system 208 may be implemented as a virtual server a public cloud computing provider (e.g., Amazon Web Services (AWS)®) of the network 211.

In an exemplary embodiment, network 210 may be a wired network, a wireless network or include one or more wired and wireless networks. For example, a network 210 may be a long-range network (e.g., wide area network (WAN), the internet, or a cellular network). Information may be sent, via network 210 using any one of various long-range wireless communication protocols (e.g., TCP/IP, HTTP, 3G, 4G/LTE, or 5G/New Radio).

In an exemplary embodiment, the patient monitoring and processing apparatus 202 may include a patient biometric sensor 212, a processor 214, a user input (UI) sensor 216, a memory 218, and a transmitter-receiver (i.e., transceiver) 222. The patient monitoring and processing apparatus 202 may continually or periodically monitor, store, process and communicate, via network 210, any number of various patient biometrics. Examples of patient biometrics include electrical signals (e.g., ECG signals and brain biometrics), blood pressure data, blood glucose data and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

Figure 4:
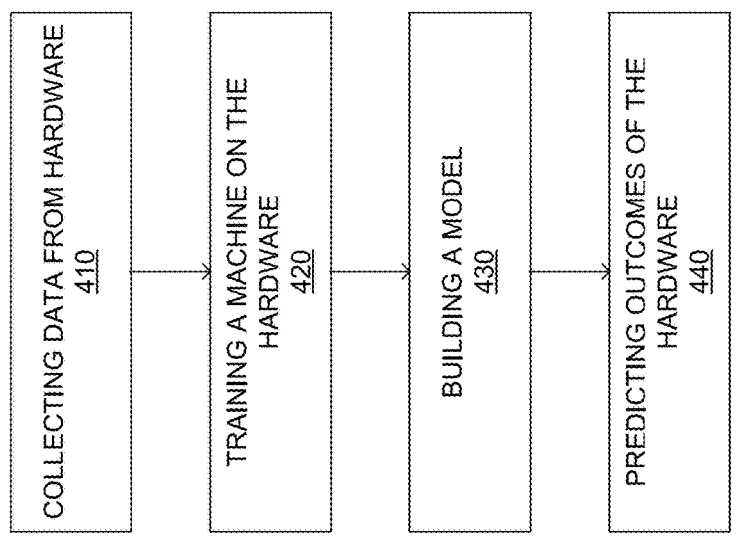
FIG. 4 illustrates a block diagram of a method performed in the artificial intelligence system of FIG. 3 according to one or more embodiments.

FIG. 3 is an artificial intelligence system 300 according to one or more embodiments. The artificial intelligence system 300 includes data 310, a machine 320, a model 330, a plurality of outcomes 340, and underlying hardware 350. FIG. 4 illustrates a block diagram of a method 400 performed in the artificial intelligence system of FIG. 3. The description of FIGS. 3-4 is made with reference to FIG. 2 for ease of understanding.

In general, the artificial intelligence system 300 operates the method 400 by using the data 310 to train the machine 320 (e.g., the local computing device 206 of FIG. 2 with the training algorithm and the autoencoder thereon) while building the model 330 to enable the plurality of outcomes 340 (to be predicted). In such a configuration, the artificial intelligence system 300 may operate with respect to the hardware 350 (e.g., the monitoring and processing apparatus 202 of FIG. 2) to train the machine 320, build the model 330, and predict outcomes using algorithms. These algorithms may be used to solve the trained model 330 and predict outcomes 340 associated with the hardware 350. These algorithms may be divided generally into classification, regression, and clustering algorithms.

At block 410, the method 400 includes collecting the data 310 from the hardware 350. The machine 320 operates as the controller or data collection associated with the hardware 350 and/or is associated therewith. The data 310 (e.g., biometric data, which may originate with the monitoring and processing apparatus 202 of FIG. 2) may be related to the hardware 350. For instance, the data 310 may be on-going data, or output data associated with the hardware 350. The data 310 may also include currently collected data, historical data, or other data from the hardware 350. For example, the data 310 may include measurements during a surgical procedure and may be associated with an outcome of the surgical procedure. For example, a temperature of a heart (e.g., of the patient 204) may be collected and correlated with an outcome of a heart procedure.

At block 420, the method 400 includes training the machine 320, such as with respect to the hardware 350. The training may include an analysis and correlation of the data 310 collected at block 410. For example, in the case of the heart, the data 310 of temperature and outcome may be trained to determine if a correlation or link exists between the temperature of the heart (e.g., of the patient 204) during the heart procedure and the outcome.

Figure 5:
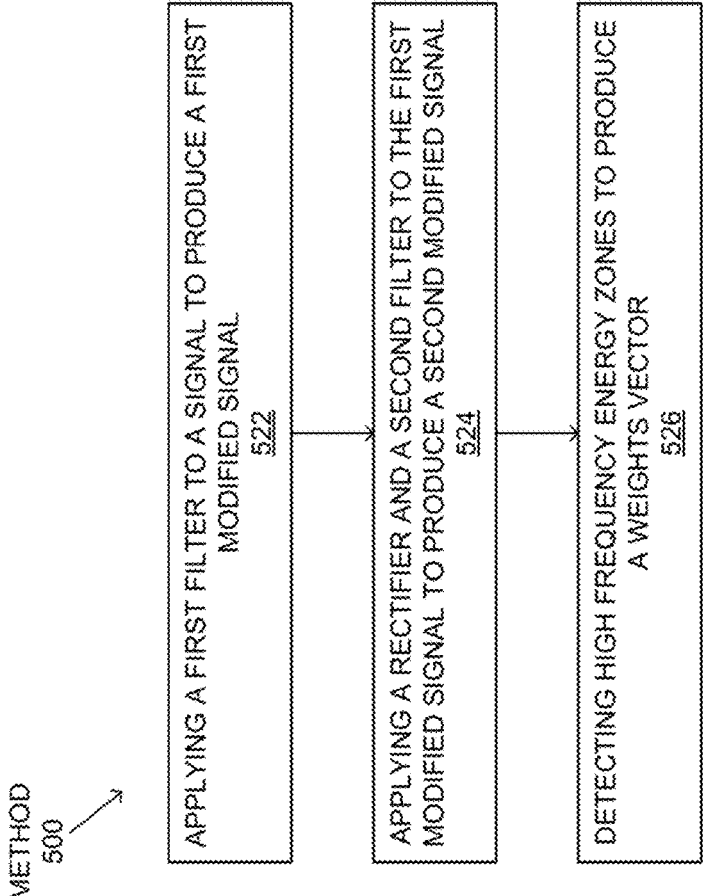
FIG. 5 illustrates a block diagram of a method according to one or more embodiments.

Turning to FIG. 5, a block diagram of a method 500 is illustrated according to one or more embodiments. The method 500 is an example of a training operation that may be employed in block 420 of FIG. 4. The training operation can include utilizing a training algorithm stored on the machine 320 to analyze and correlate the data 310 collected at block 410.

The method 500 begins at block 522, where the training algorithm applies a first filter to a signal to emphasize activity within a signal and to produce a first modified signal. At block 524, the training algorithm applies a rectifier and a second filter to the first modified signal to smooth areas of the first modified signal with clinical importance and to produce a second modified signal. At block 526, the training algorithm automatically detects high frequency energy zones of the second modified signal using an energy threshold to produce a weights vector.

The weights vector is then used as a loss function for training the algorithm. For instance, the weights vector is then utilized to build the model 330 and/or build the training dataset.

In accordance with one or more embodiments, the training algorithm applies a weighted mean square error as a loss function. In this regard in an optimization function, a neural network in its last layer reconstructs a "clean" version of intracardiac ECG signal so y is the clean version of the intracardiac ECG and $\tilde{y}$ is the output of the denoising autoencoder, the loss function in our case could be weighted mean square. More particularly, the weighted mean square error loss function can be determined according to Equation 1 given by:

$$L(\theta) = \sum_{n=0}^{N} \left[ w_n \cdot (\tilde{y_n}(\theta) - y_n)^2 \right], \qquad \text{Equation 1}$$

wherein L(θ) is the loss function, θ represents model parameters to be estimated during the training procedure, $\tilde{y_n}$ is the n'th sample of the estimated intracardiac ECG, $y_n$ is the n'th sample of intracardiac ECG signal, and $w_n$ are the n'th sample of the weights vector calculated at block 526. In accordance with one or more embodiments, other loss functions (such the weighted 0-1 loss function) can be used and are represented by Equation 2 given by:

$$L(\theta) = \sum_{n=0}^{N} [w_n \cdot l(\tilde{y_n}, y_n)], \qquad \text{Equation 2}$$

Wherein I is an indicator function according to Equation 3 given by:

$$I(\tilde{y_n}, y_n) = 0 \text{ if } \tilde{y_n} = y_n \text{ else } I(\tilde{y_n}, y_n) = 1 \qquad \text{Equation 3}$$

At block 430, the method 400 includes building the model 330 on the data 310 associated with the hardware 350. Building the model 330 may include physical hardware or software modeling, algorithmic modeling, and/or the like. This modeling may seek to represent the data 310 that has been collected and trained. According to an embodiment, the model 330 may be configured to model the operation of hardware 350 and model the data 310 collected from the hardware 350 to predict the outcome achieved by the hardware 350. In accordance with one or more embodiments, the model 330, with respect to the autoencoder, receives the raw signal data comprising signal noise, encodes the raw signal data to produce a latent representation, and decodes the latent representation to produce clean signal data reconstructed without the signal noise.

In accordance with one or more embodiments, the model 330, with respect to the training algorithm, emphasizes zones or events of clinical importance (e.g., potential origination locations of cardiac conditions) within the electrical signals. In accordance with one or more embodiments, the model 330, with respect to the autoencoder, separates between ventricular far field and atrial based activation and generate separate maps for atrial and ventricular activation.

At block 440, the method 400 includes predicting the plurality of outcomes 340 of the model 330 associated with the hardware 350. This prediction of the plurality of outcomes 340 may be based on the trained model 330. For example, and to increase understanding of the disclosure, in the case of the heart, if the temperature during the procedure is between 36.5 degrees Celsius and 37.89 degrees Celsius (i.e., 97.7 degrees Fahrenheit and 100.2 degrees Fahrenheit) produces a more favorable result from the heart procedure, the outcome can be predicted in a given procedure based on the temperature of the heart during the heart procedure. Thus, using the outcome 340 that is predicted, the hardware 350 may be configured to provide a certain desired outcome 340 from the hardware 350.

Figures 6A, 6B:
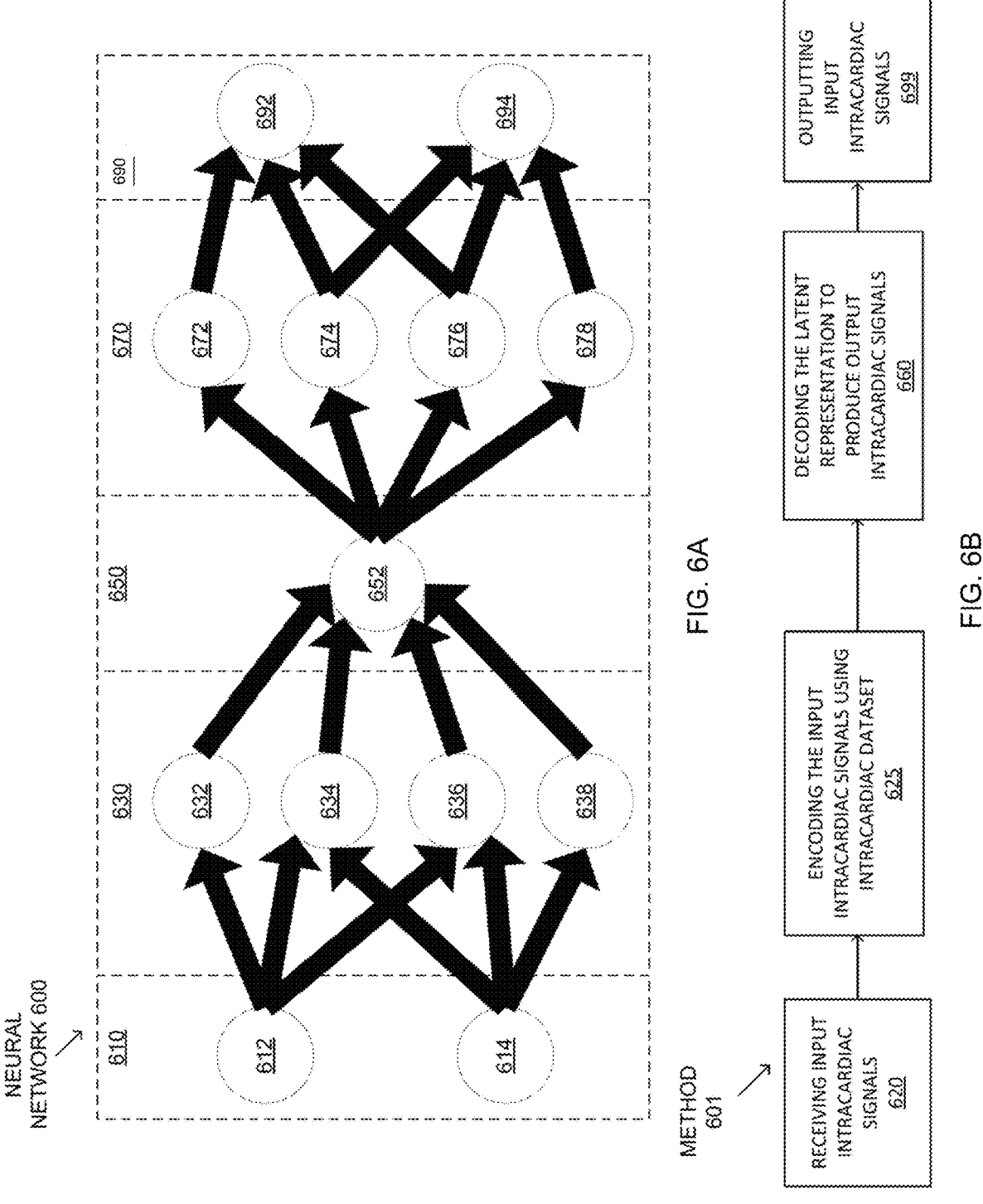
FIG. 6A illustrates an example of a neural network according to one or more embodiments.
FIG. 6B illustrates a block diagram of a method performed in the neural network of FIG. 6A according to one or more embodiments.

FIGS. 6A and 6B, collectively referred to as FIG. 6, an example of a neural network 600 (FIG. 6A) and a block diagram of a method 601 (FIG. 6B) performed in the neural network are shown according to one or more embodiments. The neural network 600 operates as an implementation of the autoencoder. The neural network 600 can be implemented in hardware, such as the machine 320 (e.g., the local computing device 206 of FIG. 2) and/or the hardware 350 (e.g., the monitoring and processing apparatus 202 of FIG. 2). In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

In most cases, the ANN is an adaptive system that changes its structure based on external or internal information that flows through the network. In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data or task makes the design of such functions by hand impractical.

Neural networks can be used in different fields. The tasks to which ANNs are applied tend to fall within the following broad categories: function approximation, or regression analysis, including time series prediction and modeling; classification, including pattern and sequence recognition, novelty detection and sequential decision making, data processing, including filtering, clustering, blind signal separation and compression.

Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis, financial applications, data mining (or knowledge discovery in databases, "KDD"), visualization and e-mail spam filtering. For example, it is possible to create a semantic profile of user's interests emerging from pictures trained for object recognition.

Returning to FIG. 6, a block diagram of a method 601 is illustrated according to one or more embodiments. The method 601 depicts operations of the neural network 600 (e.g., an autoencoder). In the neural network 600, an input layer 610 is represented by a plurality of inputs, such as 612 and 614. With respect to block 620 of the method 601, the input layer 610 receives the plurality of inputs (e.g., input intracardiac signals) as an initial operation. The plurality of inputs can be ultrasound signals, radio signals, audio signal, or a two-dimensional picture. More particularly, the plurality of inputs can be represented as input data (X), which is raw data recorded from an atria. Note that desired information lies in high frequency zones of the heart (e.g., the atrium), and the autoencoder provides a better construction of the input intracardiac signals.

At block 625 of the method 601, the neural network 600 encodes the input intracardiac signals utilizing an intracardiac dataset (e.g., produced by the training algorithm as the "clean" signal) to produce a latent representation. The latent representation includes one or more intermediary images derived from the input intracardiac signals. According to one or more embodiments, the latent representation is generated by an element-wise activation function (e.g., a sigmoid function or a rectified linear unit) of the autoencoder that applies a weight matrix to the input intracardiac signals and adds a bias vector to the result. Note that weights and biases of the weight matrix and the bias vector can be initialized randomly, and then updated iteratively during training.

The intracardiac dataset can be clean data that includes predetermined and approved signals that are free from interferences, artifacts, and noise (e.g., an example of clean). In an embodiment, the training algorithm produces one or more signals. In an embodiment, an expert medical professional, a physician, or the like can review, edit to remove signal interferences, signal artifacts, and signal noise, and approve each electrical signal of the intracardiac dataset. In an embodiment, the intracardiac data can have a number of electrical signals on the order of thousands or greater, where a signal morphology of each electrical signal is examined using template matching and blanking. Given the volume of electrical signals and the complexity of reviewing, editing, and approving, creation of the intracardiac dataset can be considered a data training portion of the multi-step data manipulation by the autoencoder.

As shown in FIG. 6, the inputs 612 and 614 are provided to a hidden layer 630 depicted as including nodes 632, 634, 636, and 638. Thus, layers 610, 630, and 650 can be considered an encoder stage that takes the plurality of inputs 612 and 614 and transfer it to a deep neural network depicted in 630 to learn some smaller representation of the input (e.g., a resulting the latent representation or data coding 652). The deep neural network could be convolutional neural networks, a long short-term memory neural network, a fully connected neural network, or combination thereof. The inputs 612 and 614 can be intracardiac ECG, ECG, or intracardiac ECG and ECG. This encoding provides a dimensionality reduction of the input intracardiac signals. Dimensionality reduction is a process of reducing the number of random variables (of the plurality of inputs) under consideration by obtaining a set of principal variables. For instance, dimensionality reduction can be a feature extraction that transforms data (e.g., the plurality of inputs) from a high-dimensional space (e.g., more than 10 dimensions) to a lower-dimensional space (e.g., 2-3 dimensions). The technical effects and benefits of dimensionality reduction include reducing time and storage space requirements for the data, improving visualization of the data, and improving parameter interpretation for machine learning. This data transformation can be linear or nonlinear. The operations of receiving (block 620) and encoding (block 625) can be considered a data preparation portion of the multi-step data manipulation by the autoencoder.

According to an embodiment, the data preparation can further include intracardiac-electrocardiograms (IC-ECG) data collection of the atria (upper chambers through which blood enters the ventricles of the heart) with simultaneous recordings from the ventricle (the two lower chambers of the heart).

At block 660 of the method 601, the neural network 600 decodes the latent representation to produce output intracardiac signals. The decoding stage takes the encoder output (e.g., the resulting the latent representation or data coding 652) and tries to reconstruct using another deep neural network 660 some form of the inputs 612 and 614. In this regard, the nodes 672, 674, 676, and 678 are combined to produce in the output layer 690 outputs 692 and 694, as shown in block 699. That is, the output layer 690 reconstruct the inputs 612 and 614 on a reduced dimension but without the signal interferences, signal artifacts, and signal noise. The output intracardiac signals 692 and 694 can be a ventricular far field estimation in the case of IC-ECGs. Other examples of the outputs 692 and 694 include Intracardiac ECG, clean version of intracardiac ECG (denoised version), ECG, and denoised ECG. The denoised version of intracardiac ECG could be free from one or more of the following: far field reduction, power line noise, contact noise, deflection noise, baseline wonders, respiration noise, and Fluro noise.

The neural network 600 performs the processing via the hidden layer 630 of the nodes 632, 634, 636, and 638 to exhibit complex global behavior, determined by the connections between the processing elements and element parameters. The target data for the output layer 650 includes target data type one ventricular activity (Y1) and includes target data type two input data after far field reduction (Y2). Note that far field causes problems with respect to generating and navigating 3D maps (e.g., ventricular far field may interfere with atrial activation). Thus, a technical effect and benefit of the autoencoder employing the neural network 600 includes improving the accuracy of 3D maps due to artifact (with respect to the far field) removal.

In accordance with one or more embodiments, a model of the autoencoder employing the neural network 600 can separate between ventricular far field and atrial based activation and generate separate maps for atrial and ventricular activation.

In accordance with an embodiment, the autoencoder can be a denoising autoencoder to find mapping functions (f, g) such that f(X)=Y1 and g(X)=Y2. Any combination of software and/or hardware (e.g., the local computing device 206 and the remote computing system 208, along with the monitoring and processing apparatus 202) can individually or collectively store, execute, and implement the denoising autoencoder and functions thereof. The denoising autoencoder trains an autoencoder to reconstruct an input from a corrupted version of itself to force the hidden layer (e.g., the hidden layer 630 of FIG. 6) to discover more robust features (i.e., useful features that will constitute better higher-level representations of the input) and prevent it from learning a particular identity (i.e., always returning to a same value). In this regard, the denoising autoencoder encodes the input (e.g., to preserve information about the input) and reverses the effect of a corruption process stochastically applied to the input of an autoencoder.

Figure 7:
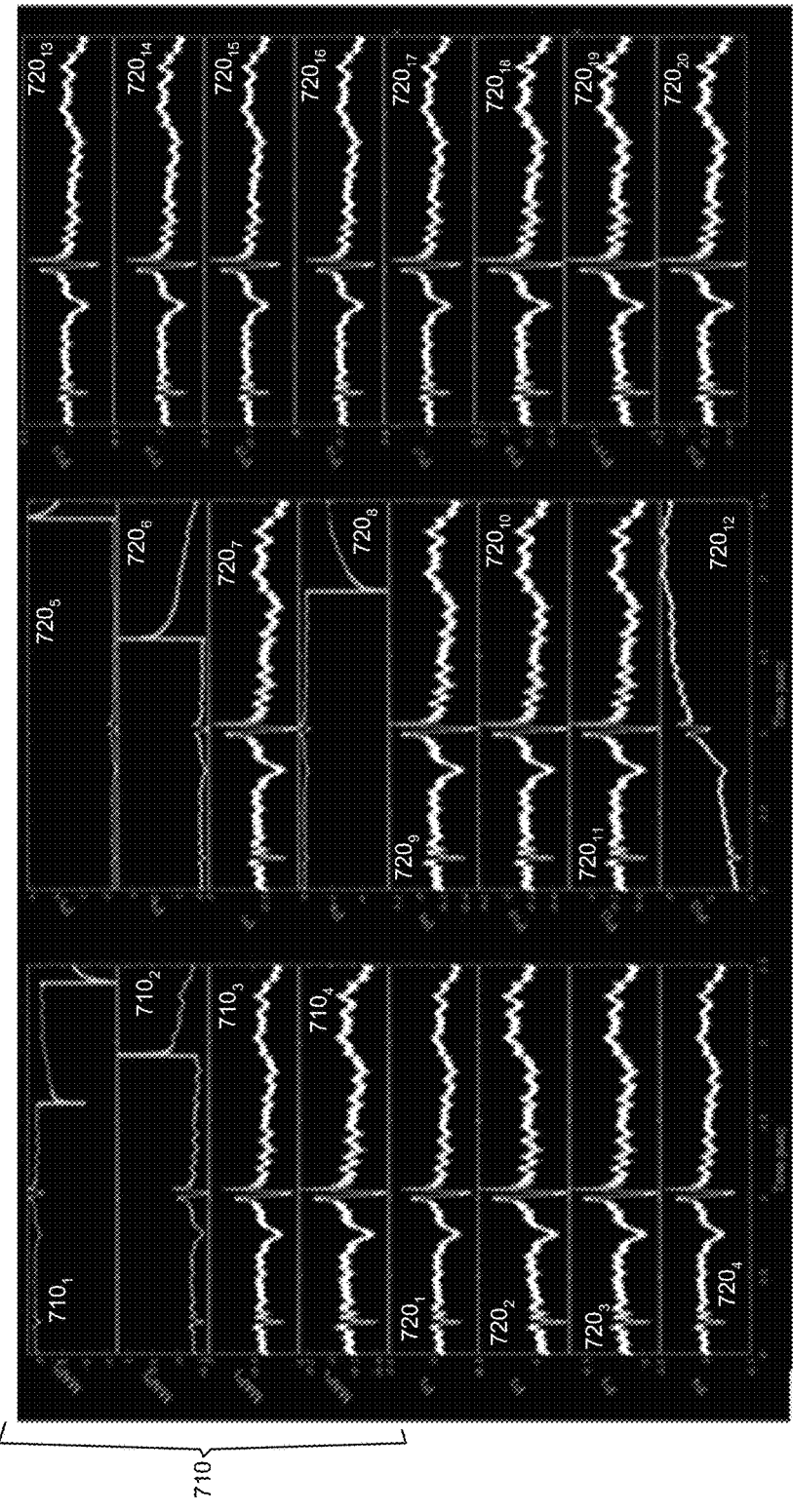
FIG. 7 illustrates contact noise examples according to one or more embodiments.

FIG. 7 illustrates contact noise examples 700 recorded in a controlled aquarium environment. Map 1-4 710 (collectively and 710₁, 710₂, 710₃, 710₄ individually) may be provided in this example as the mapping catheter. Catheters P1-P20 720 (collectively and 720₁, 720₂, 720₃, 720₄, 720₅, 720₆, 720₇, 720₈, 720₉, 720₁₀, 720₁₁, 720₁₂, 720₁₃, 720₁₄, 720₁₅, 720₁₆, 720₁₇, 720₁₈, 720₁₉, 720₂₀ individually) are provided as the penta-ray different catheters. In this illustration of examples 700, Map 1 710₁ (mapping catheter electrode 1) is touching Penta-Ray electrode 5 720₅ and 6 720₆ (P5, P6) and Map 2 710₂ touches P8 720₈ illustrating the contact noise.

Figure 8A:
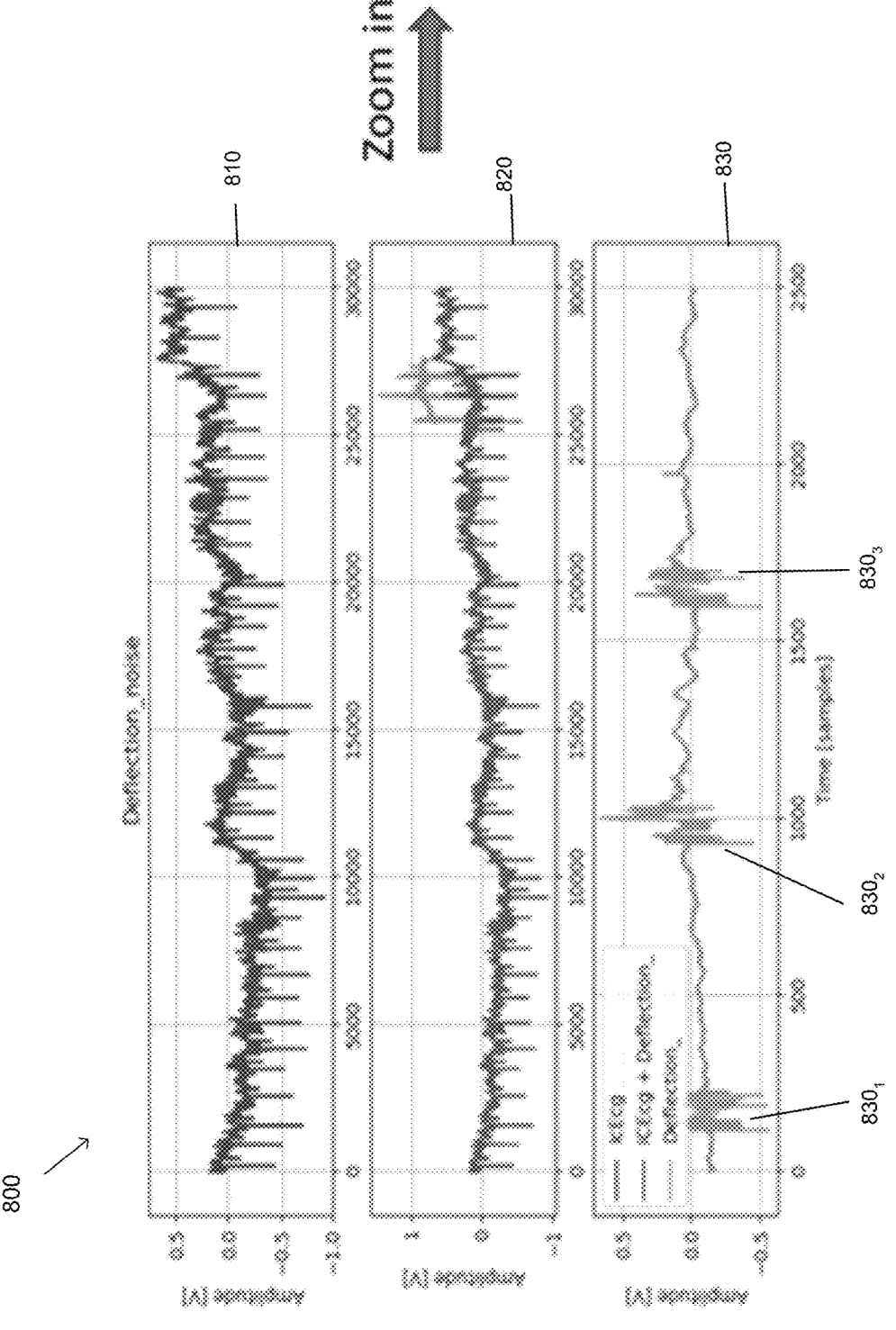
FIG. 8A illustrates deflection noise examples according to one or more embodiments.
Figure 8B:
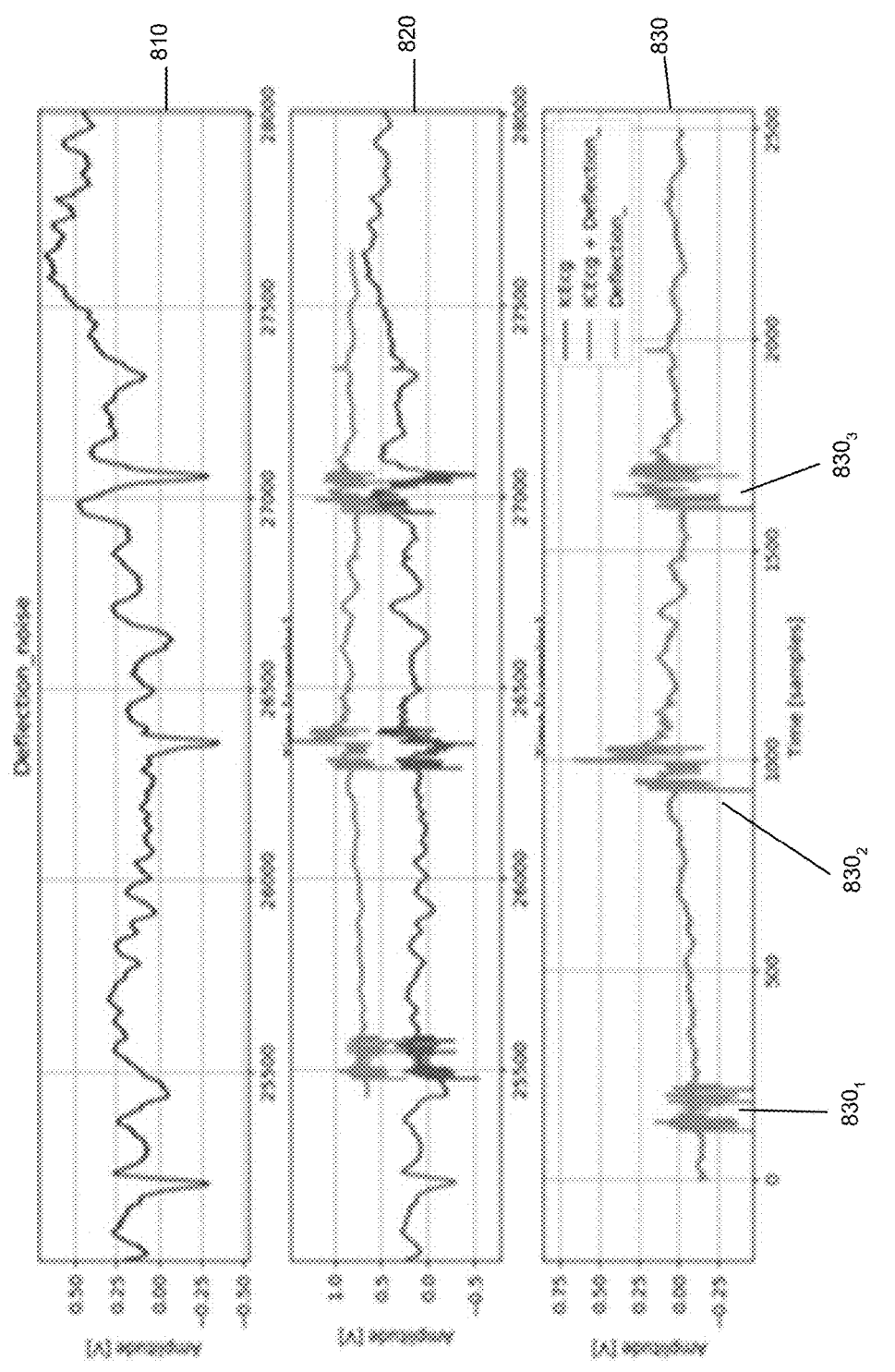
FIG. 8B illustrates deflection noise examples of FIG. 8A with an increased x-axis to zoom in on features according to one or more embodiments.

FIG. 8A illustrates deflection noise examples 800 recorded in a controlled aquarium environment. These data samples may be provided with random start times and having random durations. FIG. 8B illustrates deflection noise examples 800 of FIG. 8A with an increased x-axis to zoom in on features. In particular, the bottom plot 830 represents deflection noise recorded in an aquarium. The bottom plot 830 illustrates three high frequency bursts 8301, 8302, 8303 that indicate the three times the catheter was deflected. The upper plot 810 represents a signal free from deflection or contact noise. The middle plot 820 illustrates a signal that is the sum of deflection and contact noise.

These examples demonstrate another way to use the denoised autoencoder. The interference (contact noise, deflection noise powerline noise and etc.) is recorded and then added to a clean version of intracardiac ECG. Therefore, a denoised version and clean version of the signal is created for training purposes.

According to one or more embodiments, the denoising autoencoder implements a long short-term memory neural network architecture, a convolutional neural network architecture, or the like. The architecture of the denoising autoencoder can be configurable with respect to a number of layers, a number of connections (e.g., encoder/decoder connections), a regularization technique (e.g., dropout or BN); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The convolutional neural network architecture is a shared-weight architecture with translation invariance characteristics where each neuron in one layer is connected to all neurons in the next layer. The regularization technique of the convolutional neural network architecture can take advantage of the hierarchical pattern in data and assemble more complex patterns using smaller and simpler patterns. If the denoising autoencoder implements the convolutional neural network architecture, other configurable aspects of the architecture can include a number of filters at each stage, kernel size, a number of kernels per layer.

In an example operation according to one or more embodiments, the denoising autoencoder receives a "clean and approved" intracardiac dataset from a plurality of electrical signals. As indicated herein, an expert medical professional, a physician, or the like can review and edit the dataset to remove signal interferences, signal artifacts, and signal noise, and approve each electrical signal of the intracardiac dataset. Next, the denoising autoencoder builds a model (e.g., the model 330 of FIG. 3) from the clean and approved intracardiac dataset.

The denoising autoencoder receives input intracardiac signals, which include at least far field artifacts. The input intracardiac signals may be recorded by one or more monitoring and processing apparatuses (e.g., a penta-ray catheter with twenty electrodes, a basket catheter with sixty-four electrodes, a plurality of body surface leads, etc.). Note that far field causes problems regarding generating and navigating 3D maps (i.e., ventricular far field may interfere with atrial activation).

The denoising autoencoder encodes the input intracardiac signals using the model. This encoding provides a dimensionality reduction of the input intracardiac signals, according to how the model dictates the reduction, that remove at least far field artifacts. The result of the encoding is a production of a latent representation. This encoding provides a dimensionality reduction of the input intracardiac signals.

The denoising autoencoder decodes the latent representation to produce output intracardiac signals and maps the output intracardiac signals. For instance, the denoising autoencoder (utilizing its underlying architecture) finds mapping functions (f, g), such that f(X)=Y1 and g(X)=Y2.

ECGs are generated from the mapped output intracardiac signals. The ECGs can be generated by a computing device that is executing the denoising autoencoder or by another device. The ECGs, which are improved because the signal interference, the signal noise, and the signal artifacts are removed, can then be displayed to a physician. The improved ECGs and intracardiac ECGs dramatically reduce the time spent on each cardiac case.

As indicated herein, during intracardiac-electrogram mapping, the mapping catheter records both atrial and ventricular activations. In some cases, the ventricular far field may interfere with atrial activation (e.g., signal interference), which may affect clinical understanding and interpretation of Carto maps. In accordance with one or more embodiments, the technical effects and benefits of the denoising autoencoder include separating between ventricular far field and atrial based activation and generating separate maps for atrial and ventricular activation (e.g., the denoising autoencoder uses the model, during decoding, to separate between ventricular far field and atrial based activation within the one or more output intracardiac signals).

Figure 9:
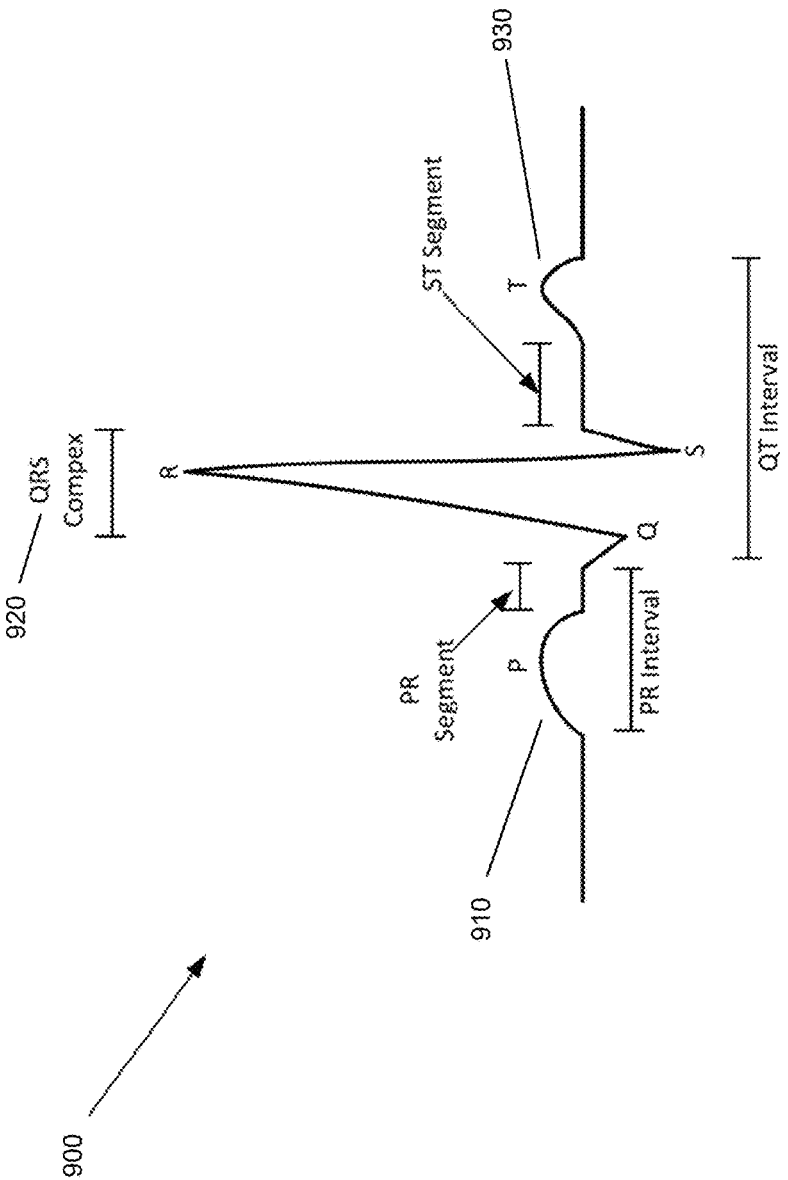
FIG. 9 illustrates a graphical depiction of a signal according to one or more embodiments.

Turning to FIG. 9, a graphical depiction of a signal 900 is illustrated according to one or more embodiments. As shown by the signal 900, an ECG signal contains a P wave 910 (due to atrial depolarization), a QRS complex 920 (due to atrial repolarization and ventricular depolarization) and a T wave 930 (due to ventricular repolarization). An ECG signal is generated by contraction (depolarization) and relaxation (repolarization) of atrial and ventricular muscles of the heart. To record an ECG signal, electrodes can be placed at specific positions on the human body or can be positioned within a human body via a catheter. Artifacts (e.g., noise) are the unwanted signals that are merged with electrical signals such as ECG signals, and sometimes create obstacles for the diagnosis and/or treatment of a cardiac condition. Artifacts in electrical signals can be baseline wander, powerline interference, EMG noise, power line noise, etc. That is, examples of artifacts include, but are not limited to, power noise (e.g., electrostatic and electromagnetic coupling between the circuitry and 50 or 60 Hz power lines), Fluro noise (e.g., fluorescent lights), contact noise (e.g., collision between catheter electrodes), and deflection noise (e.g., discharges of static electricity during catheter deflection)

Baseline wander or baseline drift occurs where the base axis (x-axis) of a signal appears to 'wander' or move up and down rather than be straight. This may cause the entire signal to shift from its normal base. In ECG signals, the baseline wander is caused due to improper electrode contact (e.g., electrode-skin impedance), patient movement, and cyclical movement (e.g., respiration).

Figure 10:
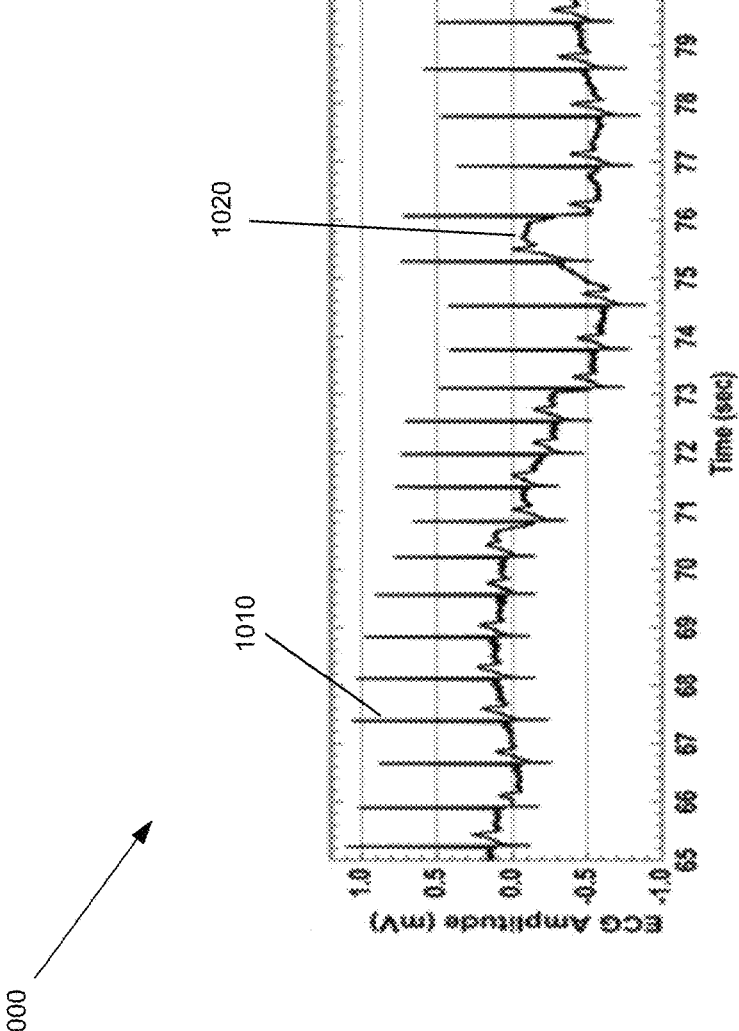
FIG. 10 illustrates a graphical depiction of a signal according to one or more embodiments.

FIG. 10 illustrates a graphical depiction of a signal 1010 is illustrated in plot 1000 according to one or more embodiments. In this regard, signal 1010 is a typical ECG signal affected by baseline wander 1020. The frequency content of the baseline wander 1020 is in the range of 0.5 Hz. Increased movement of the body during exercise or stress test increases the frequency content of baseline wander. According to implementations, given that the baseline signal is a low frequency signal, a Finite Impulse Response (FIR) high-pass zero phase forward-backward filtering with a cutoff frequency of 0.5 Hz to estimate and remove the baseline wander 1020 in the ECG signal 1010 can be used.

Electromagnetic fields caused by a powerline represent a common noise source in electrical signals such as ECGs, as well as to any other bioelectrical signal recorded from a patient's body. Such noise is characterized by, for example, 50 or 60 Hz sinusoidal interference, possibly accompanied by a number of harmonics. Such narrowband noise renders the analysis and interpretation of the ECG more difficult, since the delineation of low-amplitude waveforms becomes unreliable and spurious waveforms may be introduced. It may be necessary to remove powerline interference from ECG signals as it superimposes the low frequency ECG waves like P wave 910 and T wave 930.

Figure 11:
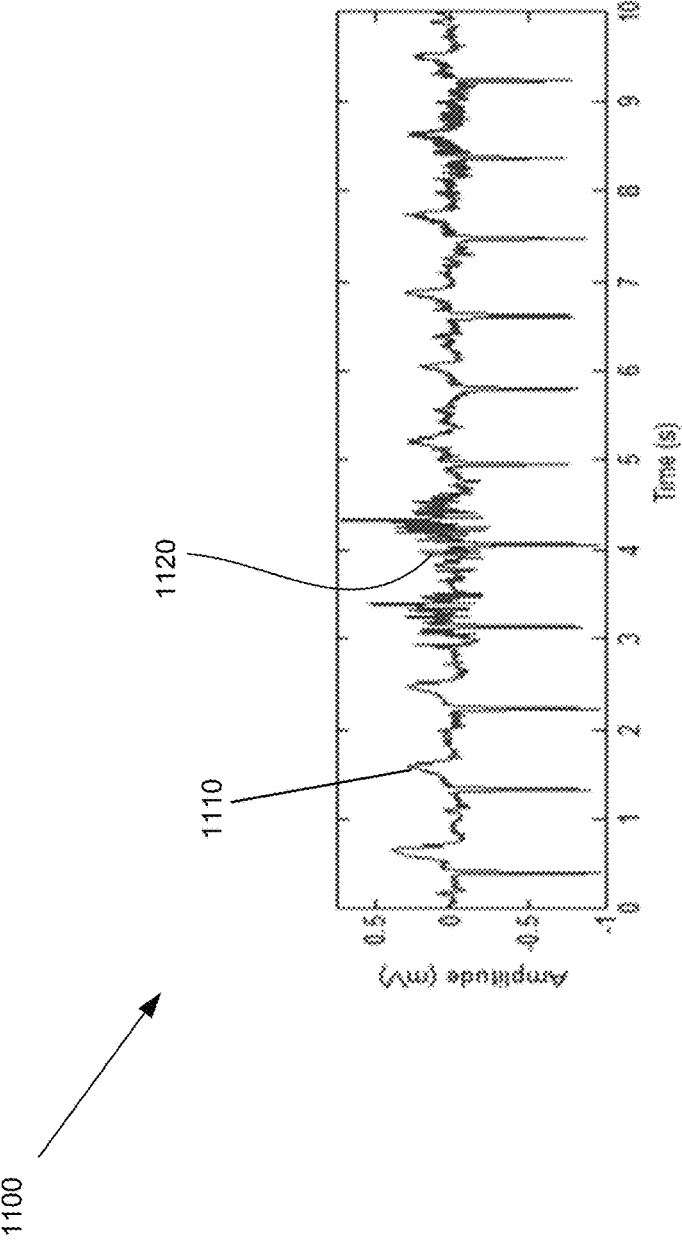
FIG. 11 illustrates a graphical depiction of a signal according to one or more embodiments.

The presence of muscle noise can interfere with in many electrical signal applications such as ECG applications, as low amplitude waveforms can become obscured. Muscle noise is, in contrast to baseline wander 1020 and 50/60 Hz interference, not removed by narrowband filtering, but presents a different filtering problem as the spectral content of muscle activity considerably overlaps that of the PQRST complex 920. As an ECG signal 1010 is a repetitive signal, techniques can be used to reduce muscle noise in a manner similar to the processing of evoked potentials. FIG. 11 illustrates a graphical depiction 1100 of a signal 1110 is illustrated according to one or more embodiments. In this regard, signal 1110 is an ECG signal interfered by an EMG noise 1120. Instruments for measuring electrical signals such as ECG signals often detect electrical interference corresponding to a line, or mains, frequency. Line frequencies in most countries, though nominally set at 50 Hz or 60 Hz, may vary by several percent from these nominal values.

Various techniques for removing electrical interference from electrical signals 1110 can be implemented. Several of these techniques use of one or more low-pass or notch filters. For example, a system for variable filtering of noise in ECG signals may be implemented. The system may have a plurality of low pass filters including one filter with a, for example, 3 dB point at approximately 50 Hz and, for example, a second low pass filter with a 3 dB point at approximately 5 Hz.

According to another example, a system for rejecting a line frequency component of an electrical signal 1110 may be implemented by passing the signal through two serially linked notch filters. A system with a notch filter that may have either or both low-pass and high-pass coefficients for removing line frequency components from an ECG signal may be implemented. The system may also support removal of burst noise and calculate a heart rate from the notch filter output.

According to another example, a system with several units for removing interference may be implemented. The units may include a mean value unit to generate an average signal over several cardiac cycles, a subtracting unit to subtract the average signal from the input signal to generate a residual signal, a filter unit to provide a filtered signal from the residual signal, and/or an addition unit to add the filtered signal to the average signal.

According to another example, an analog-to-digital (A/D) converter may provide noise rejection by synchronizing a clock of the converter with a phase locked loop set to the line frequency.

Additionally, biometric (e.g., biopotential) patient monitors may use surface electrodes to make measurements of bioelectric potentials, such as ECG or electroencephalogram (EEG). The fidelity of these measurements is limited by the effectiveness of the connection of the electrode to the patient. The resistance of the electrode system to the flow of electric currents, known as the electric impedance, characterizes the effectiveness of the connection. Typically, the higher the impedance, the lower the fidelity of the measurement. Several mechanisms may contribute to lower fidelity.

Signals from electrodes with high impedances are subject to thermal noise (or so-called Johnson noise), voltages that increase with the square root of the impedance value. In addition, biopotential electrodes tend to have voltage noises in excess of that predicted by Johnson. Also, amplifier systems making measurements from biopotential electrodes can have degraded performance at higher electrode impedances. The impairments are characterized by poor common mode rejection, which tends to increase the contamination of the bioelectric signal by noise sources such as patient motion and electronic equipment that may be in use on or around the patient. These noise sources are particularly prevalent in the operating theatre and may include equipment such as electrosurgical units (ESU), cardiopulmonary bypass pumps (CPB), electric motor-driven surgical saws, lasers and other sources.

During a cardiac procedure, it is often desirable to measure electrode impedances continuously in real time while a patient is being monitored. To do this, a very small electric current is typically injected through the electrodes and the resulting voltage measured, thereby establishing the impedance using Ohm's law. This current may be injected using DC or AC sources. It is often not possible to separate voltage due to the electrode impedance from voltage artifacts arising from interference. Interference tends to increase the measured voltage and thus the apparent measured impedance, causing the biopotential measurement system to falsely detect higher impedances than are actually present. Often such monitoring systems have maximum impedance threshold limits that may be programmed to prevent their operation when they detect impedances in excess of these limits. This is particularly true of systems that make measurements of very small voltages, such as the EEG. Such systems require very low electrode impedances.

FIG. 12 illustrates a block diagram of a method 1200 according to one or more embodiments. In accordance with an embodiment, method 1200 is implemented by an autoencoder, where the autoencoder includes a training algorithm as described herein. In accordance with one or more embodiments, the training algorithm can be considered a deep learning training loss function and, more specifically, an autoencoder clinical weighted MSE loss function. Further, the autoencoder can execute in one or more modes. For instance, a first mode can include building a dedicated graphic user interface comprising one or more filters. In the first method a dedicated GUI is built with the ability to filter out noise components manually based on set of predefined filters, (note that raw data signals are usually recorded with noise). In this way, the autoencoder experiences at least two sets of signals, such as an original signal that contains noise and a denoised signal that is used to train the autoencoder. A second mode can include recording noise in a control environment and adding the noise to the clean signal data (e.g., a clean version from previous stage). The noise can include least one of power line noise, contact noise, deflection noise, Fluro noise, and ventricular far field.

Figure 13:
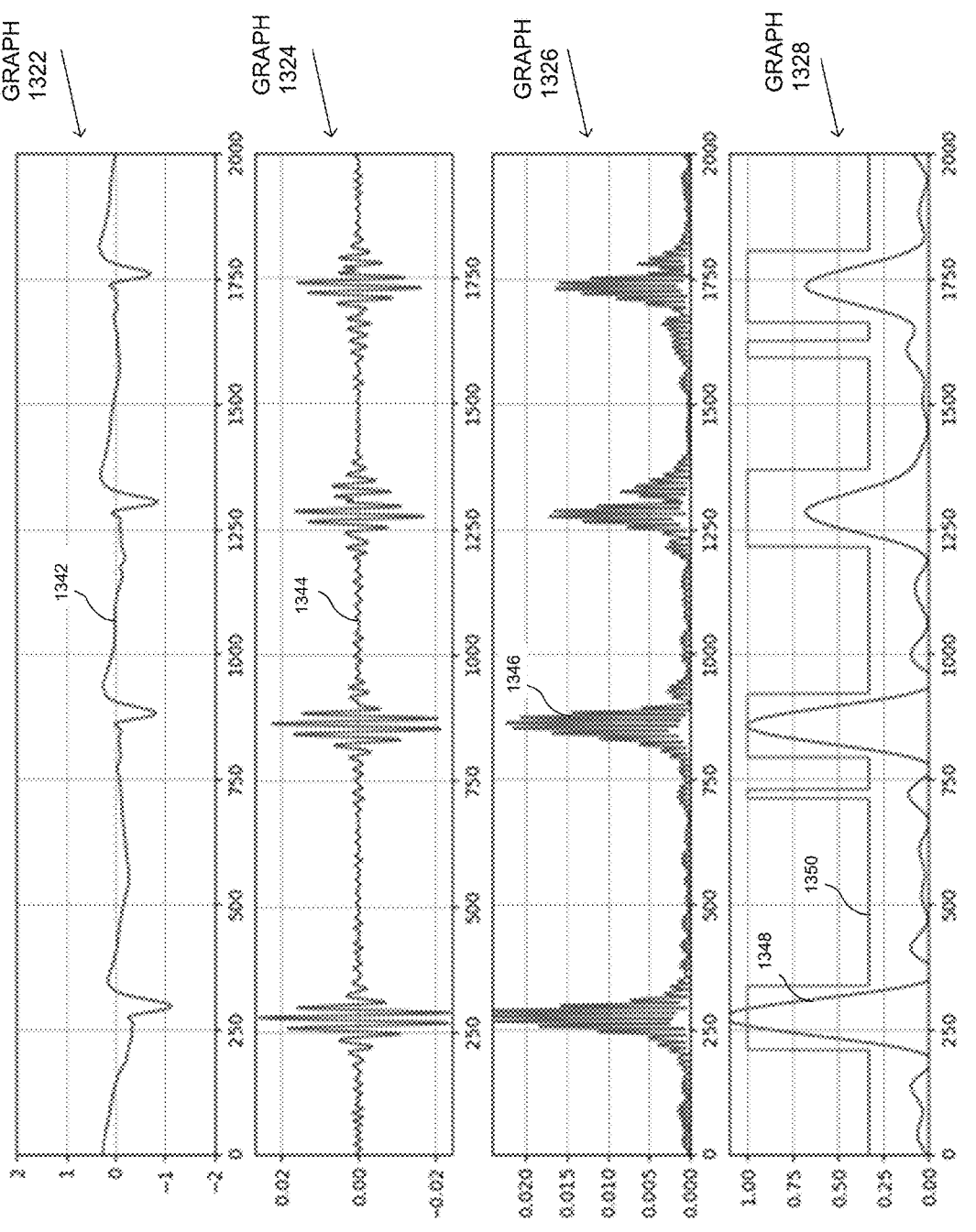
FIG. 13 illustrates a plurality of graphs indicating a signal processing by an autoencoder according to one or more embodiments.

Any combination of software and/or hardware (e.g., the local computing device 206 and the remote computing system 208, along with the monitoring and processing apparatus 202) can individually or collectively store, execute, and implement the autoencoder and functions thereof. FIG. 13 illustrates a plurality of graphs 1322, 1324, 1326, and 1328 indicating signal processing by the autoencoder (e.g., stages for the autoencoder clinical weighted MSE loss function) and/or signal processing by the training algorithm (e.g., stages for the autoencoder clinical weighted MSE loss function) according to one or more embodiments. The description of FIGS. 12-13 is collectively made for ease of understanding.

The autoencoder automatically self-trains to reconstruct an input from a corrupted version of itself. In this regard, the autoencoder forces a hidden layer therein (e.g., the hidden layer of FIG. 6) to discover more robust features (i.e., useful features that constitute better higher-level representations of the input) and prevent it from learning a particular identity (i.e., always returning to a same value). Further, the autoencoder encodes the input (e.g., to preserve information about the input) and reverses the effect of a corruption process stochastically applied to the input of an autoencoder.

Generally, in deep learning, backpropagation algorithms are used in training feedforward neural networks for supervised learning. The adjective "deep" in deep learning comes from the use of multiple layers in the network as described herein in FIG. 6. Backpropagation algorithms work by computing a gradient of a loss function with respect to each weight by the chain rule. The weights are updated to minimize a loss function. Further, gradient descent or variants, such as a stochastic gradient descent, can be used.

For instance, a deep learning neural network learns to map a set of inputs to a set of outputs from training data. The problem of learning is cast as a search or optimization problem, and an algorithm is used to navigate the space of possible model parameters that may be used to make reasonable predictions of the desired output. Typically, a neural network model is trained using the stochastic gradient descent optimization algorithm to learn a set of model parameters using the backpropagation of error algorithm. The gradient descent algorithm seeks to change the parameters of the model so that the next evaluation reduces the error, meaning the optimization algorithm is navigating down the gradient (or slope) of the loss function. In this regard, the loss function may be denoted as $L(y,\tilde{y})$ to provide a kind of a measurement of how the desired output y resembles the model output $\tilde{y}$). Examples of loss functions include, but are not limited to, MeanSquaredError class, MeanAbsoluteError class, MeanAbsolutePercentageError class, MeanSquaredLogarithmicError class, CosineSimilarity class, mean_squared_error function, mean_absolute_error function, mean_absolute_percentage_error function, mean_squared_logarithmic_error function, and cosine_similarity function. Examples of loss functions (modified to include the clinical weights function) for time series analysis include MSE functions or mean absolute error (MAE) functions. For example, the autoencoder clinical weighted MSE loss function is a multi-step data manipulation of electrical signals to detect or quantify or detect high frequency zones in a signal and then use autoencoder clinical weighted MSE loss function to enhance a signal reconstruction around atrium activity.

As indicated herein, when trying to extract or learn important features/representation (e.g., such as for classification or autoencoding of IC-ECG or body surface intracardiac-electrocardiograms BS-ECG) it is important to emphasize zones or events of clinical importance. As MSE functions, MAE functions, and/or other regression loss functions fail to emphasize zones or events of clinical importance, the training algorithm provides improved methods that emphasize zones or events of clinical importance for use with intracardiac and body surface electrocardiograms. For instance, the technical effects and benefits of the autoencoder clinical weighted MSE loss function include reducing an overall training of the IC-ECG denoising autoencoder by a factor of ten (10) and increasing the accuracy and consistency of reconstruction/denoising of the signals of the IC-ECG denoising autoencoder.

Method 1200 begins at block 1215, where the training algorithm receives a signal (see ECG signal 1342 of graph 1322 of FIG. 13). This signal can be an electrical signal from a heart that describes heart activity. The signal can be stored within the medical device equipment or provided to the medical device equipment in which the training algorithm executes. In the case of body surface ECG, signal noise of the signal (e.g., raw signal data) can include, but not limited to, baseline wander, powerline interference, movement artifact, muscle artifact, additive white Gaussian noise, etc. In the case of IcECG, signal noise of the signal (e.g., raw signal data) can include, but not limited to, power line noise, deflection noise, contact noise, ventricular far field noise, Fluro nose, additive white Gaussian noise, etc.

At block 1220, the training algorithm applies a first filter to a signal to emphasize activity within a signal and to produce a first modified signal. The first filter can be a high pass filter (e.g., implemented through hardware and/or software within the medical device equipment) that passes portions of the ECG signal 1342 with a frequency higher than a predetermined cutoff frequency and attenuates portions of the ECG signal 1342 with frequencies lower than the predetermined cutoff frequency. The activity emphasized by the training algorithm includes atrial or ventricle activity or zones along the ECG signal 1342 with (atrial/ventricular) activity. In accordance with one or more embodiments, the predetermined cutoff frequency can be set to 40 Hz (e.g., see a high pass 40 Hz signal 1344 of graph 1324 of FIG. 13 as the first modified signal).

At block 1230, the training algorithm applies a rectifier to the first modified signal to produce a second modified signal. The rectifier (e.g., implemented through hardware and/or software within the medical device equipment) converts an alternating current of the first modified signal into a direct one by allowing a current to flow through it in one direction only. In accordance with one or more embodiments, the second modified signal is shown as rectified signal 1346 of graph 1326 of FIG. 13.

At block 1235, the training algorithm applies a second filter to the second modified signal to produce a third modified signal. The second filter can be a low pass filter (e.g., implemented through hardware and/or software within the medical device equipment) that passes portions of the rectified signal 1346 with a frequency lower than a predetermined cutoff frequency and attenuates portions of the rectified signal 1346 with frequencies higher than the predetermined cutoff frequency. The second first of the training algorithm smooths areas with clinical importance (e.g., see a normalized low pass signal 1348 of graph 1328 of FIG. 13 as the third modified signal). Clinical importance can include origination locations of cardiac conditions.

At block 1240, the training algorithm automatically detects high frequency energy zones of the third modified signal using an energy threshold to produce a fourth modified signal (e.g., see a signal 1350 of graph 1328 of FIG. 13). In other words, zones with high energy are clinically detected using a threshold of energy, such that when energy is above a certain value then there is atrial activity. The threshold of energy, energy threshold, and/or certain value can be a predetermined data setting of the training algorithm. In accordance with one or more embodiments, the energy threshold can be set to 10%.

At block 1250, the training algorithm applies weighted vector derived from a ratio. In accordance with one or more embodiments, the ratio is 1:P (P>1), such that a weight in zones with "atrial or ventricular" activity is P times higher than "quiet" zones of the BS-ECG or IC ECG. For instance, when 1:P=1:3, wherein 1 is a high energy and 3 is a low energy, errors of symptoms around the atrial activity will be three times higher than atrial zones. In using weighted MSE for learning, the weight is based on the signal itself.

At block 1260, method 1200 includes adding the clean signal to a training dataset. The training algorithm builds the training dataset comprising at least the clean signal. The training dataset can be built into any data structure (e.g., data organization, management, and storage format) that enables efficient access, modification, and use of the clean signal. The data structure can be stored in a memory of the medical device equipment as described herein. In accordance with one or more embodiments, the training dataset can include a clean data version with optimal filters. The training algorithm can record part of the signal noise separately and randomly add the signal noise back to the training dataset.

At block 1270, method 1200 includes training an autoencoder using the training dataset. The training algorithm directly teaches the autoencoder how to find cardiac condition in intracardiac signals using the training dataset. At block 1280, method 1200 includes generating an electrocardiogram from one or more output intracardiac signals, outputted by the trained autoencoder using an intracardiac dataset as described herein.

In accordance with one or more embodiments, the autoencoder can include a unique cost function (with clinical meaning) to overcome "artificial" signals. A stack of LSTM layers connected to a dense layer is used to detect a type of noise and quality of intracardiac signal. In turn, the autoencoder "denoise" the intracardiac signal if a quality of the intracardiac signal is above certain threshold. The autoencoder can denoise all noise types. When using a multiple-electrode approach (e.g., with different types of diagnostic and therapeutic catheters), embodiments herein can use a neural network to "denoise" the signals of microelectrodes. The neural network can be based on deep learning autoencoders as described herein.

In accordance with one or more embodiments, the autoencoder includes two parts: an encoder and a decoder. The encoder maps an input (e.g., IcECG signals) to a hidden representation (u) via a nonlinear transformation. The decoder maps the hidden representation back to reconstructed data via another nonlinear transformation, as shown in Equation 4 and Equation 5:

$$u = f(\text{noisy IcECG,encoder}) \qquad \text{Equation 4,}$$

$$\text{clean IcECG} = g(u,\text{decoder}) \qquad \text{Equation 5}$$

In accordance with one or more embodiments, the denoised autoencoder may be trained based on a loss function that emphasizes atrial activity. The loss function utilizes a neural network where a last layer reconstructs a clean signal data. The loss function may be a weighted mean square error loss function $L(\theta)$ according to equation 6, where $\theta$ represent model parameters to be estimated during the training procedure, $\widetilde{y_n}$, is the n'th sample of the estimated IcECG, $y_n$ is the n'th sample of IcECG signal, and $w_n$ are weights. An automated process can define the weights in Equation 6:

$$(\theta) = \sum_{n=0}^{N} \left[ w_n \cdot (\widetilde{y_n}(\theta) - y_n)^2 \right] \qquad \text{Equation 6}$$

Figure 14:
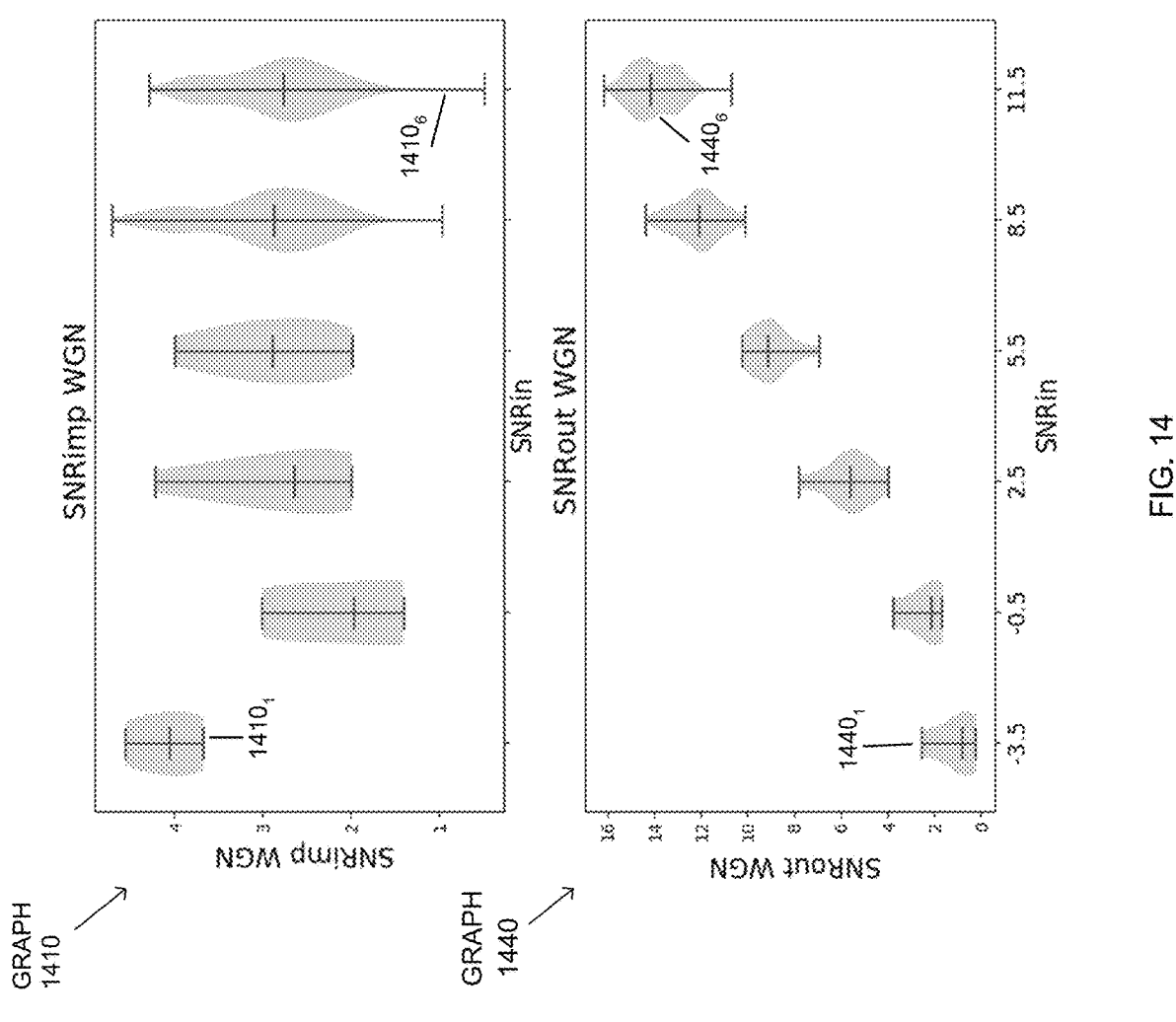
FIG. 14 illustrates a plurality of graphs according to one or more embodiments.

The hidden representation (u) is taught using noisy IcECG signals. In teaching the neural network, a clean IcECG signal is initially generated by filtering out, from an actual IcECG signal, power line interference, baseline wander due to respiration, and high frequency noise which is typically due to muscle contraction. Noisy IcECG signals may be generated by adding these types of noise into the clean signal in a randomized manner. In some cases, white Gaussian noise can be added. FIG. 14 illustrates a plurality of graphs 1410 and 1440 according to one or more embodiments. Graph 1410 illustrates a signal to noise (SNR) ratio for an input, while graph 1440 illustrates a SNR ratio for an output. If the SNR input is low at point 1410₁ in graph 1410, then the SNR out is low at point 1440₁ in graph 1440. Despite the SNR output being low, there is still an improvement in the signals as the autoencoder is cleaning the signal and providing the improvement. This improvement is illustrated in the smaller SNR of point 1440₁ as compared to point 1410₁. If the SNR input is higher at point 1410₆ (compared to point 1410₁) in graph 1410, then the SNR out is higher at point 1440₆ (compared to point 1440₁) in graph 1440. Despite the SNR output being higher, there is still an improvement in the signals as the autoencoder is cleaning the signal and providing the improvement. This improvement is illustrated in the smaller SNR of point $1440_6$ as compared to point $1410_6$. The SNR improvement (imp) is an SNR output minus an SNR input.

The technical effects and benefits include a denoising autoencoder with a cost function with clinical meaning, detecting different types of IcECG noises, and estimating a quality of expected denoised signal to mark as noise signals with low quality.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a WTRU, UE, terminal, base station, RNC, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:

receiving raw signal data comprising signal noise, the signal noise at least including far field artifacts;

encoding, by a denoised autoencoder, the raw signal data by performing a denoising autoencoder operation that reduces dimensionality of the received raw signal data to produce a latent representation with at least the far field artifacts removed, the latent representation being generated by an element-wise activation function that applies a weight matrix to the received raw signal data; and decoding, by the denoised autoencoder, the latent representation to produce clean signal data reconstructed without the signal noise.

2. The method of claim 1, wherein the raw signal data includes at least one of power line noise, contact noise, deflection noise, Fluro noise, and ventricular far field.

3. The method of claim 1, wherein the denoised autoencoder executes in a mode to build a dedicated graphic user interface comprising one or more filters.

4. The method of claim 1, wherein the denoised autoencoder executes in a mode to record noise in a control environment and add the noise to the clean signal data.

5. The method of claim 1, wherein the raw signal data comprises electrical signals of a heart from N channels of intracardiac electrocardiograms, intracardiac electrocardiograms and body surface electrocardiograms, or intracardiac electrocardiograms with a position of each electrode and anatomy information.

6. The method of claim 1, wherein the denoised autoencoder is trained based on a loss function that emphasizes atrial activity.

7. The method of claim 6, wherein the loss function utilizes a neural network where a last layer reconstructs a clean signal data.

8. The method of claim 6, wherein the loss function comprises a weighted mean square error loss function.

9. The method of claim 1, wherein a patient biometric sensor of a monitoring and processing apparatus records the raw signal data.

10. The method of claim 1, wherein the denoising autoencoder operation comprises passing the raw signal data through a deep neural network to reduce a dimensionality of the raw signal data and to retain important information.

11. The method of claim 1, wherein the latent representation comprises a reduced dimensionality and important information from the raw signal data.

12. The method of claim 1, wherein the clean signal data comprises input intracardiac signals reconstructed minimizing the signal noise.

13. The method of claim 1, wherein the denoised autoencoder learns the clean signal data to denoise subsequent raw intracardiac signals during the denoising autoencoder operation.

14. The method of claim 13, wherein the denoised autoencoder detects noise type and quality of the subsequent raw intracardiac signals.

15. The method of claim 14, wherein the denoised autoencoder performs the denoising autoencoder operation on the subsequent raw intracardiac signals based on whether the quality is above a threshold.

16. The method of claim 1, wherein the method further comprises generating an electrocardiogram from the clean signal data, the electrocardiogram being substantially free from the signal noise.

17. A system comprising:

a memory storing processor executable code for a denoised autoencoder; and one or more processors coupled to the memory, the one or more processors configured to execute the processor executable code to cause:

receiving raw signal data comprising signal noise, the signal noise at least including far field artifacts;

encoding, by the denoised autoencoder, the raw signal data by performing a denoising autoencoder operation that reduces dimensionality of the received raw signal data to produce a latent representation with at least the far field artifacts removed, the latent representation being generated by an element-wise activation function that applies a weight matrix to the received raw signal data; and decoding, by the denoised autoencoder, the latent representation to produce clean signal data reconstructed without the signal noise.

\* \* \* \* \*